US011776004B1

(12) United States Patent
Garner, IV et al.

(10) Patent No.: US 11,776,004 B1
(45) Date of Patent: Oct. 3, 2023

(54) SYSTEMS AND METHODS FOR GEOLOCATION-BASED CITY AND COMMUNITY PROMOTED AUGMENTED REALITY REWARDS

(71) Applicant: Wells Fargo Bank, N.A., San Francisco, CA (US)

(72) Inventors: Andrew J. Garner, IV, State Road, NC (US); Chris Theodore Kalaboukis, San Jose, CA (US); Rameshchandra Bhaskar Ketharaju, Hydedrabad (IN); Joon Maeng, Newcastle, WA (US); Andres J. Saenz, Redmond, WA (US); Ramanathan Ramanathan, Bellevue, WA (US); Abhijit Rao, Irvine, CA (US)

(73) Assignee: Wells Fargo Bank, N.A., San Francisco, CA (US)

( * ) Notice: Subject to any disclaimer, the term of this patent is extended or adjusted under 35 U.S.C. 154(b) by 0 days.

(21) Appl. No.: 17/147,286

(22) Filed: Jan. 12, 2021

(51) Int. Cl.
| | |
|---|---|
| *G06Q 30/00* | (2023.01) |
| *G06Q 30/0207* | (2023.01) |
| *H04W 4/021* | (2018.01) |
| *G16Y 40/60* | (2020.01) |
| *H04W 4/80* | (2018.01) |
| *G06Q 30/0238* | (2023.01) |

(Continued)

(52) U.S. Cl.
CPC ..... *G06Q 30/0239* (2013.01); *G06Q 30/0215* (2013.01); *G06Q 30/0236* (2013.01); *G06Q 30/0238* (2013.01); *G16Y 40/60* (2020.01); *H04W 4/021* (2013.01); *H04W 4/80* (2018.02); *A61B 5/01* (2013.01); *A61B 5/08* (2013.01)

(58) Field of Classification Search
CPC .... H04W 4/80; H04W 4/021; G06Q 30/0236; G06Q 30/0238
See application file for complete search history.

(56) References Cited

U.S. PATENT DOCUMENTS

| | | |
|---|---|---|
| 8,684,922 B2 | 4/2014 | Tran |
| 8,862,448 B2 | 10/2014 | Holmes et al. |
| 9,285,589 B2 | 3/2016 | Osterhout et al. |

(Continued)

OTHER PUBLICATIONS

Google gets patent for redirection of a document URL to a natively-operating application, Jun. 21, 2016, Global IP News Software Patent News (Year: 2016).*

*Primary Examiner* — Matthew L Hamilton
(74) *Attorney, Agent, or Firm* — Foley & Lardner LLP

(57) ABSTRACT

Systems, methods, and apparatuses for facilitating rewards are described herein. The system includes internet of things (IoT) devices associated with each of a plurality of users. A reward computing system includes input/output (I/O) devices configured to receive sensor data associated with an environment. The reward computing system is configured to generate a location data and/or an entity positioning data set associated with at least one of the plurality of users and based on the sensor data. The computing system is also configured to determine a behavior of each of the plurality of users. The reward computing system is also configured to generate a plurality of reward tokens and associate the reward tokens with one or more of the plurality of users and based on at least one of the location data set, the entity positioning data set and the behavior of the plurality of users.

20 Claims, 14 Drawing Sheets

(51) Int. Cl.
*A61B 5/01* (2006.01)
*A61B 5/08* (2006.01)

(56) References Cited

U.S. PATENT DOCUMENTS

| | | | |
|---|---|---|---|
| 9,460,263 | B2 | 10/2016 | Holmes et al. |
| 9,727,912 | B1 | 8/2017 | Poursartip et al. |
| 9,786,005 | B1 | 10/2017 | Poursartip et al. |
| 9,907,730 | B2 | 3/2018 | Macoviak et al. |
| 10,060,802 | B1 | 8/2018 | Ragosta et al. |
| 10,529,017 | B1 | 1/2020 | Gianakopoulos |
| 10,606,353 | B2 | 3/2020 | Coleman et al. |
| 11,080,981 | B1* | 8/2021 | Gochoo ............. G08B 21/0492 |
| 11,094,420 | B1* | 8/2021 | Nadikattu .............. G06N 20/00 |
| 2002/0169871 | A1* | 11/2002 | Cravo de Almeida ...................... H04L 43/0817 709/224 |
| 2008/0294546 | A1 | 11/2008 | Flannery |
| 2010/0131390 | A1 | 5/2010 | Emswiler |
| 2014/0297006 | A1* | 10/2014 | Sadhu .................... G01S 19/17 700/91 |
| 2014/0330103 | A1 | 11/2014 | Yoo |
| 2014/0344854 | A1* | 11/2014 | Kanojia ............... H04N 21/233 725/34 |
| 2015/0073996 | A1* | 3/2015 | Makhotin .......... G06Q 20/3227 705/71 |
| 2016/0078781 | A1 | 3/2016 | McCartney |
| 2016/0106627 | A1 | 4/2016 | Geman et al. |
| 2016/0234647 | A1* | 8/2016 | Macdonald ........... H04W 4/027 |
| 2016/0301723 | A1* | 10/2016 | Sinclair ................. H04L 65/765 |
| 2017/0053091 | A1 | 2/2017 | Holmes et al. |
| 2017/0112407 | A1 | 4/2017 | Wu |
| 2017/0173262 | A1 | 6/2017 | Veltz |
| 2017/0323485 | A1 | 11/2017 | Samec et al. |
| 2018/0053200 | A1* | 2/2018 | Cronin ............... G06Q 30/0239 |
| 2018/0247023 | A1 | 8/2018 | Divine et al. |
| 2018/0276618 | A1* | 9/2018 | Nichani ............. G06Q 10/1053 |
| 2018/0308585 | A1 | 10/2018 | Holmes et al. |
| 2018/0349986 | A1 | 12/2018 | Fidanza et al. |
| 2018/0374582 | A1 | 12/2018 | Holmes et al. |
| 2019/0096526 | A1 | 3/2019 | Hirsch et al. |
| 2019/0384392 | A1 | 12/2019 | Aimone et al. |
| 2020/0098461 | A1 | 3/2020 | Macoviak et al. |
| 2020/0118164 | A1 | 4/2020 | Defrank et al. |
| 2020/0356897 | A1 | 11/2020 | Diggle et al. |
| 2021/0202067 | A1* | 7/2021 | Williams ............. A61B 5/4845 |
| 2021/0327249 | A1* | 10/2021 | Levin ................. G08B 21/0236 |
| 2021/0374891 | A1* | 12/2021 | Menon ................. H04W 4/029 |
| 2021/0385783 | A1* | 12/2021 | Xu ........................ H04W 76/11 |
| 2021/0407690 | A1* | 12/2021 | Locke ................. G06Q 50/265 |
| 2022/0067984 | A1 | 3/2022 | Choi |
| 2022/0208391 | A1* | 6/2022 | Mekid .................... G16H 50/80 |

\* cited by examiner

US 11,776,004 B1

SYSTEMS AND METHODS FOR GEOLOCATION-BASED CITY AND COMMUNITY PROMOTED AUGMENTED REALITY REWARDS

TECHNICAL FIELD

The present disclosure relates to systems and methods for geolocation-based city and community promoted augmented reality rewards.

BACKGROUND

Rewards are a convenient way for businesses to provide consumers with a benefit for socially responsible behavior. Typically, rewards are given for customer loyalty or as incentives for buying a particular product or service. Rewards can also be used in community settings to encourage socially responsible behavior, such as physical distancing during epidemics. However, individuals do not actively seek out and register on reward platforms unless they are already socially conscious. As such, providing individuals with a streamlined way to register for community-promoted rewards and offering "previews" of the individual's baseline behavior and target state may increase individual interest in socially responsible behavior.

SUMMARY

At least one arrangement relates to a system for facilitating rewards. The system includes a plurality of internet of things (IoT) devices. At least one of the plurality of IoT devices is associated with each of a plurality of users. The system also includes a reward computing system that has a plurality of input/output (I/O) devices configured to receive sensor data associated with an environment. The reward computing system is configured to generate a location data set associated with at least one of the plurality of users, based on the sensor data. The reward computing system is also configured to generate an entity positioning data set associated with at least one of the plurality of users, based on the sensor data. The reward computing system is also configured to generate a plurality of reward tokens. Each of the plurality of reward tokens is associated with at least one of the plurality of users and based on at least one of the location data set and the entity positioning data set.

Another arrangement relates to a method of facilitating rewards for socially responsible behavior within an environment. The method includes identifying a first Internet of Things (IoT) device within the environment. The method also includes receiving a first behavior data associated with the first IoT device. The first behavior includes at least one of a first geo-location data and a first entity positioning data. The method also includes determining a first reward based on the first behavior data. The method also includes associating the first reward with the first IoT device.

Another arrangement relates to non-transitory computer-readable storage media having instructions stored thereon that, when executed by at least one processing circuit, cause the at least one processing circuit to perform operations to provide rewards for socially responsible behavior. The operations comprise detecting a first internet of things (IoT) device in an environment. The operations further comprise receiving a first entity positioning data associated with the first IoT device. The first entity positioning data includes at least one of a position of the first IoT device and a first health data associated with a first user of the first IoT device. The operations further comprise selectively generating at least one reward token based on the first entity positioning data. The operations further comprise associating the at least one reward token with the first IoT device. The operations further comprise facilitating a transaction. The transaction includes selectively converting the first reward token for at least one of a cash value and a discount.

This summary is illustrative only and is not intended to be in any way limiting.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Figure 1:
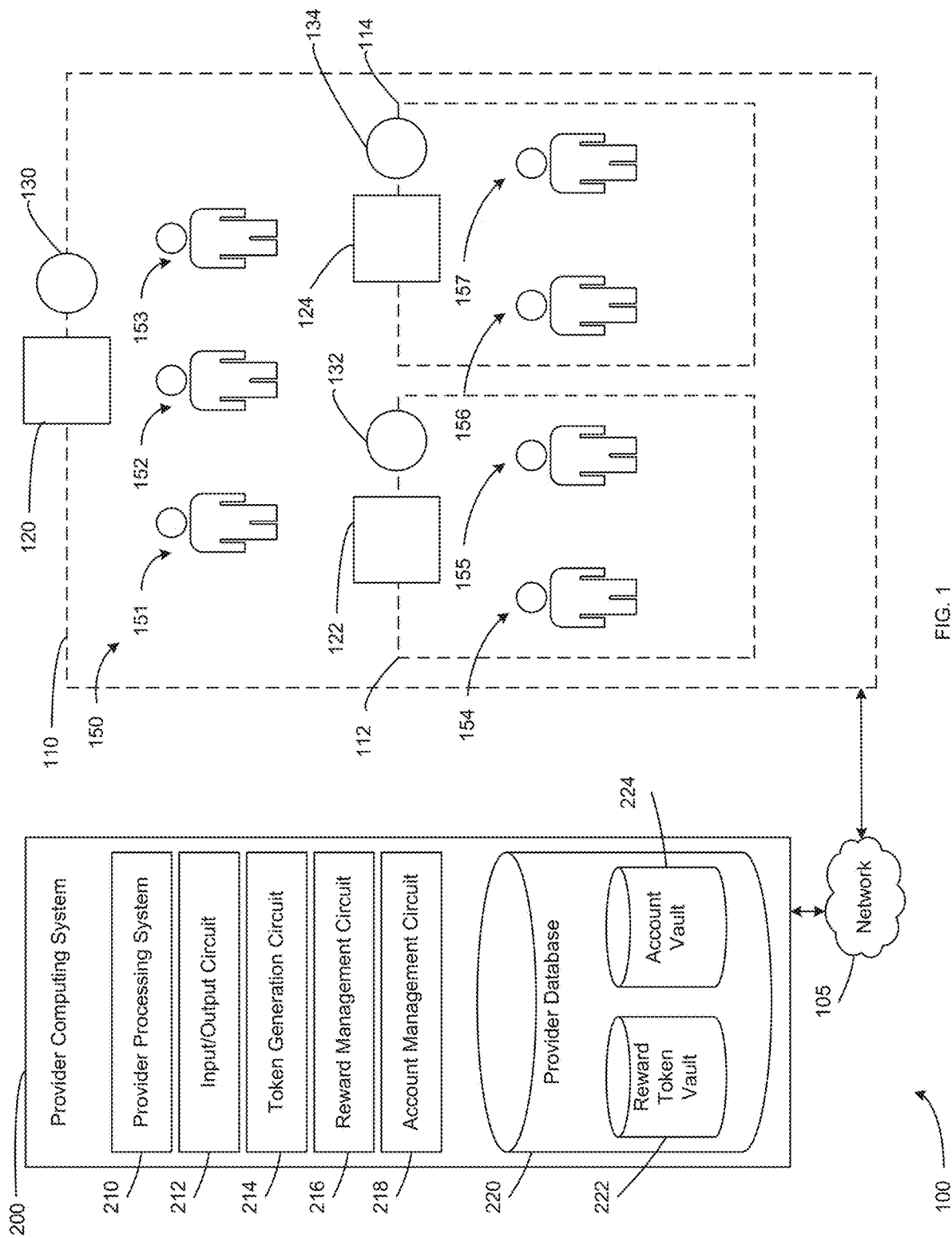
FIG. 1 is a block diagram of a system including an environment for providing rewards, according to an example arrangement.

Before turning to the figures, which illustrate certain example arrangements in detail, it should be understood that the present disclosure is not limited to the details or methodology set forth in the description or illustrated in the figures. It should also be understood that the terminology used herein is for the purpose of description only and should not be regarded as limiting.

Referring generally to the figures, systems and methods for geolocation-based city and community promoted augmented reality rewards are disclosed. The systems and methods described herein enhance the practice of providing rewards for socially responsible behavior by utilizing one or more sensors structured to sense geo-location data and/or entity positioning data of users within an environment. The sensors can be coupled to a computing system configured to determine the behavior of one or more of the users based on the geo-location data and/or the entity positioning data such that the computing system can determine a reward for each of the users based on the user behavior.

Individuals do not actively seek out and register on reward platforms that reward socially responsible behavior unless the individuals are already socially conscious. Also, few individuals will seek out and remember to carry health status monitoring transponders, physical distancing monitoring transponders, or the like. Accordingly, a technical problem emerges of how to build a rewards infrastructure for socially responsible behavior using existing common device platforms, such as smart phones, which most individuals routinely carry with them. Another technical problem is providing a streamlined way for individuals to register on a rewards platform by automatically delivering certain "preview"-related executables to an individual's device and then generating a subset of data, using the individual's device, to encourage the individual to register. In some arrangements described further herein, this problem is solved by allowing an individual to scan a quick response (QR) code upon entering a particular area (e.g., a store), thereby activating a "preview" executable (e.g., a light version) of a reward tracker application. The reward tracker application can accumulate rewards while the individual is in the particular area. The reward information can be communicated to a point-of-sale computing system, which may be structured to calculate and/or display the reward amount to the individual. The individual's computing device can then be caused to prompt the individual to register with the rewards system.

Yet another technical problem is ensuring that if the individual decides to de-register or not to register in the first place, the individual's personal information and collected location, health and other tracking information, which may be collected by the "preview"-related executables, is safely discarded (e.g., fully de-associated from the rewards system.)

Further, the arrangements of the reward system as described herein improve reward systems technology by performing certain steps that cannot be done by conventional reward systems or human actors. For example, the reward system may reduce the number of transmissions necessary to match a reward with a user by determining a particular reward that is relevant to the user based on the user's behavior collected locally on a user's computing device.

Further, the arrangements of the reward system may address the problem of providing user-readable notifications using limited screen space on small-screen computing devices, such as smart phones. The system may generate various user interfaces based on the user behavior. That is, the reward system may generate user interfaces with color coded icons or images indicating information relevant to the user and based on the user's behavior. Furthermore, the system may make the displayed information relevant to a particular user to ensure user engagement by determining a product relevant to a user based on the user's behavior. The system may provide a reward related to the product to the user based on the user's behavior. In some arrangements, the system may provide a better reward (e.g., a reward having more cash value) for better behavior. In some arrangements, the system may provide icons on the display of a user device. The icons may indicate situations of the user and potential actions the user may take. The icons may be color coded to further indicate which potential actions would be considered to demonstrate socially responsible behavior. For example, the system may provide one or more icons indicating a path the user may take to a destination. The system may provide a reward to the user if the user follows a particular predetermined socially responsible path to the destination. In some arrangements, the reward system may also utilize augmented reality (AR) user interfaces and displays to provide the generated user interfaces.

Referring generally to the Figures, systems and methods for geolocation-based, city and community promoted augmented reality rewards are provided herein. The systems and methods are directed towards a reward platform for rewarding users for socially responsible behavior. According to various exemplary arrangements, the rewards platform defines an environment and obtains behavior data associated with various users within the environment. The rewards platform provides rewards to the users based on the behavior data. In some arrangements one or more of the users are registered with the rewards platform. In some arrangements, all users are registered with the rewards platform.

In an example illustrative scenario, a provider computing system may sense (e.g., identify using signals received from sensors positioned in or near an environment) an internet of things (IoT) device. The IoT device may be a user device such as a smart phone, a smart watch, etc. or an entity positioning device. The entity positioning device may be provided by a business, a community and/or a local, regional, or national government. For example, in a store, the entity positioning device may be a transponder or a sticker affixed to a shopping basket or shopping cart. The provider computing system may receive data associated with the IoT device. The data may include a geo-location of a user and/or the IoT device. The geo-location may be relative to other IoT devices, other users, stationary objects, geo-fences, and the like. The data may also include entity positioning data associated with the user. The entity positioning data may include location data, health data, and the like. The health data may include respiration data, temperature data, and the like. The provider computing system may determine, based on the data, a behavior of the user. Accordingly, the provider computing system may selectively generate and/or associate a reward token for the user based on the behavior of the user. In some arrangements, the provider computing system may generate a better reward token for socially responsible behavior. In some arrangements, the provider computing system may not generate a reward token for undesirable behavior.

FIG. 1 is a block diagram of a system 100 for providing rewards, according to an example arrangement. The system 100 includes an environment 110 and a provider computing system 200 which are communicably coupled to a network 105. The network 105 is any suitable Local Area Network (LAN) or Wide Area Network (WAN). For example, the network 105 can be supported by Frequency Division Multiple Access (FDMA), Time Division Multiple Access (TDMA), Code Division Multiple Access (CDMA) (particularly, Evolution-Data Optimized (EVDO)), Universal Mobile Telecommunications Systems (UMTS) (particularly, Time Division Synchronous CDMA (TD-SCDMA or TDS), Wideband Code Division Multiple Access (WCDMA), Long Term Evolution (LTE), evolved Multimedia Broadcast Multicast Services (eMBMS), High-Speed Downlink Packet Access (HSDPA), and the like), Universal Terrestrial Radio Access (UTRA), Global System for Mobile Communications (GSM), Code Division Multiple Access 1× Radio Transmission Technology (1×), General Packet Radio Service (GPRS), Personal Communications Service (PCS), 802.11X, ZigBee, Bluetooth, Wi-Fi, any suitable wired network, combinations thereof, and/or the like. The network 105 is structured to permit the exchange of data, values, instructions, messages, and the like between the provider computing system 200 and the environment 110 and components and/or devices thereof.

As shown, the environment 110 has one or more sensors 120, and a network circuit 130. The environment 110 may also define an environment physical perimeter and have one or more users 150 within the physical perimeter. As shown, users 151, 152, 153, 154, 155, 156, and 157 are within the environment 110. The environment 110 may also include one or more sub-environments or areas. As shown the environment 110 includes a first area 112 defining a first physical perimeter and a second area 114 defining a second physical perimeter. The first area 112 has one or more sensors 122 and a network circuit 132. As shown, users 154 and 155 are within the first area 112. The second area 114 has one or more sensors 124 and a network circuit 134. As shown, users 156 and 157 are within the second area 114. In some arrangements, the environment 110 does not include any sub-environments.

In some arrangements, the environment 110 defines a large area such as a city or a portion of the city, and the like. In some arrangements, the environment 110 defines a smaller area such as a park, a shopping mall, a strip mall, a building, and the like. For example, the environment 110 may define an area of a small portion of a city including at least one building with at least one sub-environment (e.g., first area 112 and second area 114) each defining a business within the environment 110.

In some arrangements, the environment 110 and/or sub-environments 112, 114 may be associated with a provider and/or a business. For example, the environment 110 may be associated with a provider such as an owner of a shopping mall, a local government, a financial institution, and the like. The sub-environments 112, 114 may be associated with a physical location of particular business such as a grocery store, a bank, etc.

The sensors 120, 122, and 124 are sensing devices that are configured to sense data associated with the users 150. In some arrangements, the sensors 120, 122, 124 are configured to sense data of each of the users 150. For example, the sensors 120, 122, 124 may be cameras configured to capture one or more images of each of the users 150 within the environment 110. The images may include visual data such that a computing device could determine (e.g., by utilizing computer vision methods) one or more characteristics of the users 150. In some arrangements, the sensors 120, 122, and 124 are configured to receive a signal from an IoT device (e.g., smart phone, smart wearable device, RFID tag, biometric security scanners, etc.) within the environment 110. For example, one or more of the users 150 may be associated with an IoT device, and the sensors 120, 122, and 124 may be configured to receive a signal from each of the IoT devices. In some arrangements, the signal may include the data associated with each of the users 150. The data may include one or more characteristics of each of the users 150 such as geo-location data, health data, user financial data, and the like. In some arrangements, the sensors 120, 122, 124 are configured to continuously sense the data at a predetermined interval (e.g., 1 millisecond, 10 milliseconds, 50 milliseconds, etc.).

The network circuits 130, 132, 134 are configured to provide a suitable network (e.g., a 4G network, a 5G network, etc.) for devices within the environment 110, the first area 112, and the second area 114, respectively. In some arrangements, the network circuits 130, 132, 134 are configured to be communicably coupled to the sensors 120, 122, 124. The network circuits 130, 132, 134 may receive data associated with the users 150 from the sensors 120, 122, 124. In some arrangements, the network circuits 130, 132, 134 are configured to facilitate edge computing such that the data associated with the users 150 can be stored, analyzed, etc. by the network circuits 130, 132, 134. For example, the network circuit 132 can receive a first data set associated with the first area 112 set from the one or more sensors 122. The network circuit 132 may be configured to determine, based on the first data set, one or more characteristics of the users (e.g., users 154, 155) that are within the first area 112. The network circuit 132 may also be configured to determine a behavior of the users within the first area 112 based on the one or more characteristics.

Each of the users 150 may be associated with one or more IoT devices. In some arrangements, the IoT devices may be user devices (e.g., smart phones, smart watches, etc.) and/or entity positioning devices (e.g., a custom hardware device, a wearable device, an RFID tag, etc.). In some arrangements, a provider provides the IoT device by, for example, affixing the IoT device to a user's shopping cart or shopping basket, providing a user with a wrist band comprising IoT device circuitry, etc. In some arrangements, the user provides the IoT device. For example, the user's smart phone, smart watch or another wearable device can serve as an IoT device. In another example, the user's physical transportation pass, museum pass, employee ID card, etc. may have thereon IoT device circuitry.

The provider computing system 200 includes a provider processing system 210, an input/output circuit 212, a token generation circuit 214, a reward management circuit 216, an account management circuit 218, and a provider database 220.

The provider processing system 210 is composed of a processor and a memory device. The processor can be implemented with a general-purpose processor, an Application Specific Integrated Circuit (ASIC), one or more Field Programmable Gate Arrays (FPGAs), a Digital Signal Processor (DSP), a group of processing components, or other suitable electronic processing components. The memory can be implemented with a Random Access Memory (RAM), Read-Only Memory (ROM), Non-volatile RAM (NVRAM), Flash Memory, hard disk storage, cloud storage, and other suitable electronic storage devices. The memory stores data and/or computer code for facilitating at least some of the various processes described herein. The memory includes tangible, non-transient volatile memory, or non-volatile memory. The memory stores programming logic that, when executed by the processor, controls the operations of the processing system 210 and/or other circuits and/or databases of the provider computing system 200.

The provider processing system 210 is configured to receive data associated with the users 150. In some arrangements, the data may be from the sensors 120, 122, 124. In these arrangements, the provider processing system 210 may determine, based on the data, one or more characteristics of the users 150 and/or a behavior of one or more of the users 150. In some arrangements, the data may be from the network circuits 130, 132, 134. In some arrangements, one or more of the network circuits 130, 132, 134 have already determined one or more characteristics of the users 150 and/or a behavior of one or more of the users 150. In some arrangements, the provider processing system 210 may verify the accuracy of the determination made by the network circuits 130, 132, 134. For example, provider processing system 210 may determine a behavior (or verify the determination of the behavior) of one or more of the users 150. The behavior of the one or more users 150 may include a geo-location, entity position characteristics including a health characteristic (e.g., a temperature, a respiration pattern, etc.), and the like. In some arrangements, the health characteristics also includes a determination of whether a user is wearing a face mask and whether the user is the user is correctly wearing the face mask. In these arrangements, the determination is based on the respiration pattern of the user, an image of the user, and/or data from a specialized sensor. In some arrangements, the provider processing system 210 is configured to output a behavior data associated one or more of the users 150. The behavior data includes the determination of the behavior of the one or more of the users 150.

In some arrangements, socially responsible behavior is based on predetermined behavior parameters. The behavior parameters may be different for each of the environments (e.g., the environment 110, the first area 112, and the second area 114). Additionally, the behavior parameters may be set by a user associated with the environment 110, the first area 112, and/or the second area 114. In some arrangements, the behavior data associated with the users 150 includes a distance between each of the users 150, temperature data and/or respiration data associated with each of the users 150, and an indication if one or more of the users 150 is wearing a mask properly. In some arrangements the behavior data includes interactions between the users 150 (e.g., customers) and business team members associated with the environment 110, the first area 112, and/or the second area 114.

The input/output circuit 212 is configured to receive input (e.g., from a user, an external device, etc.) and provide an output (e.g., graphics, sound, tactile feedback, etc.). In this regard, the input/output circuit 212 structured to exchange data, communications, instructions, etc. with the environment 110. In these arrangements, the input/output circuit 212 may be configured as a network interface. The network interface is structured for sending and receiving data over the network 105. Accordingly, the network interface includes any of a cellular transceiver (for cellular standards such as 5G), local wireless network transceiver (for 802.11X, ZigBee, Bluetooth, Wi-Fi, or the like), wired network interface, a combination thereof (e.g., both a cellular transceiver and a Bluetooth transceiver), and/or the like.

In some arrangements, the input/output circuit 212 includes or is coupled to an input/output device such as but not limited to, a display device, touchscreen, keyboard, microphone, and/or the like. In some arrangements, the input/output circuit 212 includes communication circuitry for facilitating the exchange of data, values, messages, and the like between the input/output circuit 212 and the components of the environment 110 such as the sensors 120, 122, 124 and/or the network circuits 130, 132, 134. In some arrangements, the input/output circuit 212 includes machine-readable media for facilitating the exchange of information between the input/output device and the components of the environment 110. In still another arrangement, input/output circuit 212 includes any combination of hardware components (e.g., a touchscreen), communication circuitry, and machine-readable media.

The token generation circuit 214 is configured to selectively generate reward tokens. The reward tokens may be configured to be redeemable in a transaction. For example, the reward tokens may include a coupon, a cash value, a voucher for a free item, a gift certificate, etc. that is redeemable in a transaction. In some arrangements, the token generation circuit 214 may generate reward tokens based on predefined parameters such as a discount percentage for a coupon, a cash amount, eligible free items, gift certificate value, etc. In some arrangements, the predefined parameters are defined by a provider team member. In some arrangements, the predefined parameters are defined by a business or other entity associated with the environment 110 and/or the sub-environments 212, 214. In some arrangements, the token generation circuit 214 is substantially similar to the provider processing system 210. In some arrangements, the token generation circuit 214 is part of the provider processing system 210.

The reward management circuit 216 is configured to manage the one or more reward tokens generated by the token generation circuit 214. In some arrangements, the reward management circuit 216 is configured to associate (e.g., electronically couple) the one or more reward tokens with one or more of the IoT devices within the environment 110. In these arrangements, the one or more IoT devices are associated with one or more of the users 150, and the reward management circuit 216 may associate the one or more reward tokens with one or more of the IoT devices based on the behavior of the one or more users 150. For example, the reward management circuit 216 may associate a first reward token with a first IoT device, the first IoT device associated with a first user (e.g., user 151) based on the user 151 having a first behavior. In some arrangements, the reward management circuit 216 is configured to associate the one or more reward tokens with a user account associated with the provider computing system 200 and one or more of the users 150 based on the behavior of the one or more users 150. For example, the reward management circuit 216 may associate a second reward token with a second user account that is associated with a second user (e.g., user 152) based on the second user 152 having a second behavior.

In some arrangements, the reward management circuit 216 is configured to facilitate redeeming the one or more reward tokens in a transaction after the one or more reward tokens are associated with an IoT device, a user account, or both. For example, a point-of-sale (POS) computing device associated with the environment 110 and/or one or more of the sub-environments (e.g., first area 112 and second area 114) may facilitate a transaction that includes a request to redeem one or more reward tokens. The reward management circuit 216 may receive the request from the POS computing device (e.g., via the network 105) and facilitate redeeming the one or more reward tokens. The reward management circuit 216 is configured to de-associate (e.g., electronically de-couple) the one or more reward tokens with the IoT device, the user account or both after the one or more reward tokens are redeemed.

The account management circuit 218 is configured to create and manage user accounts associated with the provider computing system 200 and one or more of the users 150. In some arrangements, account management circuit 218 receives a request from one or more users 150 to create a user account. In some arrangements, the request is received from a user device via the network 105. In some arrangements, the request is received from an IoT device (e.g., a computing device, a POS computing device, etc.) associated with the environment 110 and/or one or more of the sub-environments (e.g., first area 112 and second area 114). For example, the account management circuit 218 may receive a first request from a first user 151 via a user device and the network 105 to create a first user account associated with the first user. The account management circuit 218 may create the first user account responsive to the first request. In some arrangements, the account management circuit 218 is configured to associate the behavior data of one or more of the users 150 with the user accounts associated with the one or more users 150. For example, the account management circuit 218 may receive a first behavior data of the first user 151 from the provider processing system 210 and associate data related to the behavior of the first user 151 with the first user account.

In some arrangements, the account management circuit 218 is configured to create a user account that is configured to send and/or receive data from a financial account (e.g., an account associated with a financial institution) associated with one or more of the users 150. In some arrangements, the user account that is configured to selectively interface with the financial account such that the user account has limited access to the financial account.

In some arrangements, the account management circuit 218 is configured to communicate with one or more IoT devices within the environment 110. In some arrangements, the account management circuit 218 is configured to generate a hyperlink and provide the hyperlink to the one or more IoT devices. In some arrangements, the hyperlink is provided as a scannable code (e.g., a QR code). In some arrangements, the hyperlink is configured to provide a link to a user application for the reward system 100. In some arrangements, the hyperlink is configured to provide a link to a user account creation portal. In some arrangements, the hyperlink is unique for each of the users 150.

The provider database 220 is configured store data associated with the provider computing system 200 and/or the environment 110 (and/or first area 112 and second area 114) The provider database includes a reward token vault 222 and an account vault 224. The provider database 220, the reward token vault 222, and the account vault 224, the databases may be implemented as an electronic structure(s) suitable for storing information, including, for example, one or more persistent electronic structures, such as one or more, electronic file(s), data mart(s), distributed ledger(s) and the like. The data stored in the account vault 220, the reward token vault 222, and the provider database 224 of the provider computing system 200 may be stored in a multidimensional form such that the structure of the data storage entity has two dimensions (e.g., a look-up table having indexed data) or more (e.g., a relational database, a multi-dimensional database, an online analytical processing (OLAP) cube, etc.).

The reward token vault 222 is configured to store reward token data. In some arrangements, the reward token vault 222 is configured to store information that includes types of reward tokens that the token generation circuit 214 can generate. In some arrangements, the reward token vault 222 is configured to store one or more pre-generated reward tokens that the reward management circuit 216 can utilize to associate with an IoT device, a user account, or both. According to various arrangements, a reward token can include an alphanumeric string. In some arrangements, the alphanumeric string can be parsed to include any of a user identifier, user device identifier, user transceiver circuitry identifier, a reward descriptor, a reward amount, an associated merchant/organization, an associated financial institution, etc. In some arrangements, a reward token has a predetermined denomination (e.g., in dollars, points, etc.) In some arrangements, a reward token further includes a link to an AR definition schema for the corresponding reward. For example, the AR definition schema may include an image file, an audio file executable code, etc. The AR definition schema may be applied when it is detected that the token needs to be rendered to the user (e.g., visually or audibly displayed) in an AR or immersive environment. In some arrangements, for example, the AR definition schema can be referenced when the reward token is displayed on a map.

The account vault 224 is configured to store user account data. In some arrangements, the account vault 224 is configured to store all user accounts created by the account management circuit 218. In some arrangements, the account vault 224 is configured to store information that includes an association between reward tokens and user accounts. In some arrangements, the account vault 224 is configured to be accessed and modified by the reward management circuit 216 when the reward management circuit 216 facilities redeeming a reward token and de-associates the reward token form a user account.

Figure 2:
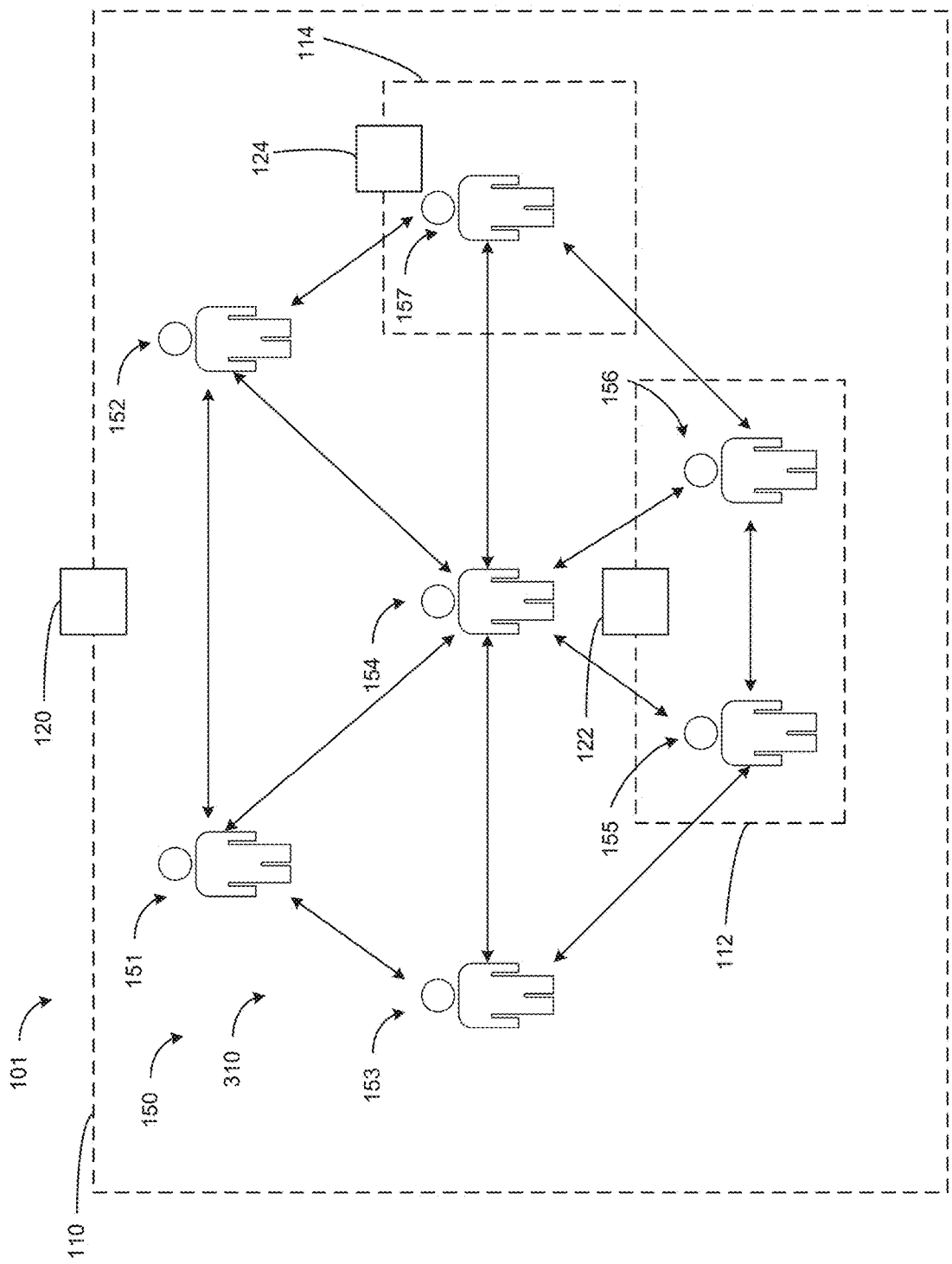
FIG. 2 is a block diagram showing an aspect related to a mesh network of the environment of the system of FIG. 1, according to a second example arrangement.

FIG. 2 is a block diagram showing an aspect related to a mesh network 310 of the environment 110 of the system 100 of FIG. 1, according to a second example arrangement. In some arrangements, environment 110 includes one or more sensors 120 as described above. Additionally, the environment 110 includes one or more sub-environments shown as first area 112 and second area 114. The first area 112 includes one or more sensors 122, as described above. The second area 114 includes one or more sensors 124, as described above. The environment 110 also includes one or more users 150 shown as users 151, 152, 153, 154, 155, 156, 157. As shown, users 155 and 156 are within the first area 112 and user 157 is within the second area 114. In some arrangements, each of the users 150 is associated with at least one IoT device.

In some arrangements, the environment 110 also includes a mesh network 310. The mesh network 310 includes each of the IoT devices associated with the users 150. In these arrangements, each of the IoT devices is configured to sense data associated with each of the users 150 and provide the data to the mesh network 310. In some arrangements, the data sensed by the mesh network 310 may include one or more of a position of the IoT devices and/or entity positioning as described above. The position of the IoT devices may be a potion relative to other IoT devices, a position relative to a predetermined stationary point, a position relative to an object, etc. The entity positioning data may include health data such as temperature data, respiration data, etc., as described above.

In some arrangements, the mesh network 310 is configured to communicably couple to one or more of the sensors 120, 122, 124 such that the mesh network 310 can send and/or receive data associated with the users to/from the sensors 120, 122, 124. In these arrangements, the mesh network 310 can provide the data to a computing system (e.g., the provider computing system 200 of FIG. 1) such that the computing system can analyze the data. In some arrangements, the mesh network 310 is configured to determine, based on the data a behavior of one or more of the users 150.

Figure 3:
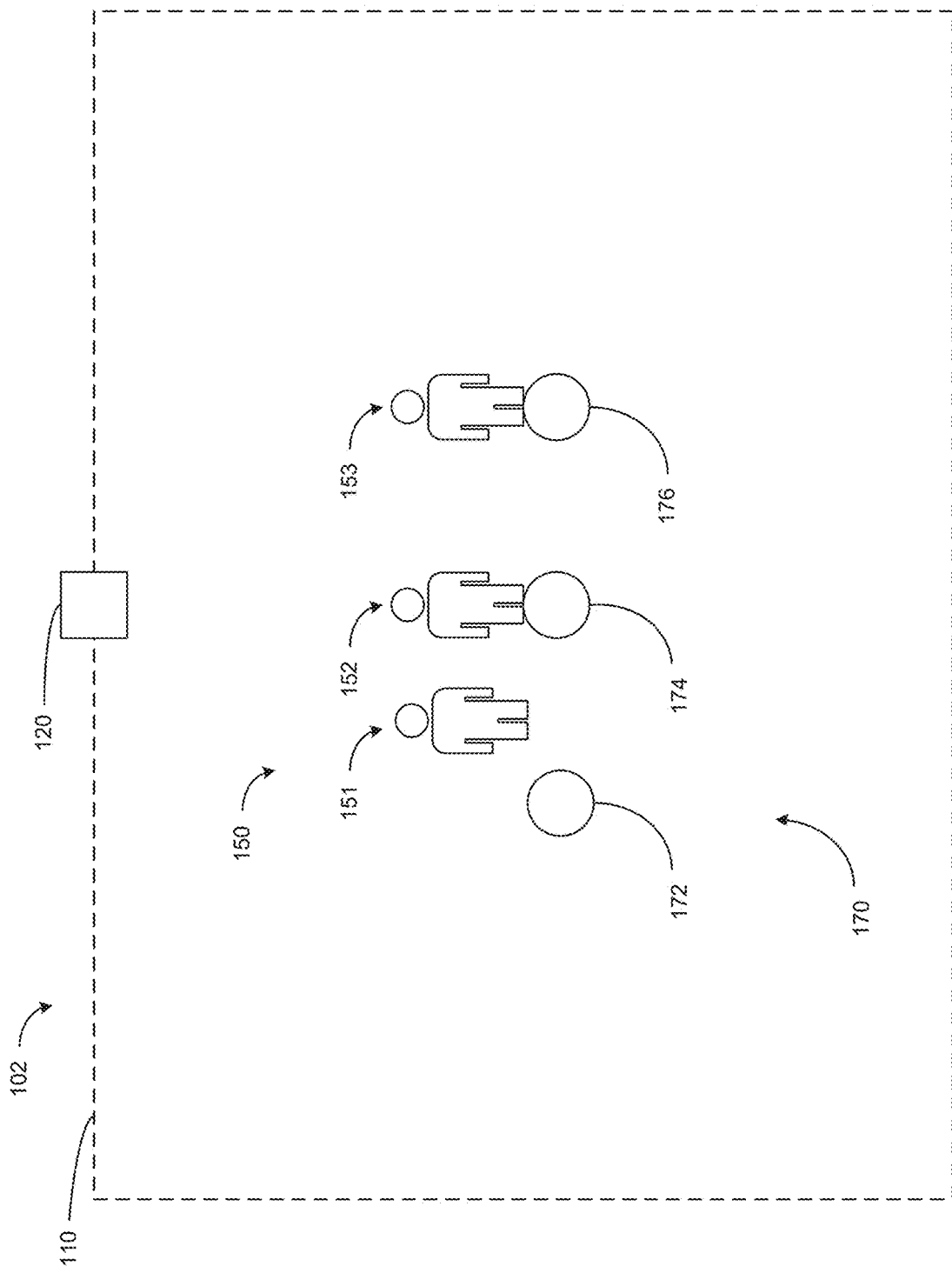
FIG. 3 is a block diagram showing an aspect related to positionable entity tracking devices of the environment of the system of FIG. 1, according to a third example arrangement.

FIG. 3 is a block diagram showing an aspect related to positionable entity tracking devices 170 of the environment 110 of the system 100 of FIG. 1, according to a third example arrangement. In some arrangements, environment 110 includes one or more sensors 120 as described above. The environment 110 also includes one or more users 150 shown as a first user 151, a second user 152, and a third user 153. In some arrangements, each of the users 150 are associated with at least one IoT device.

In some arrangements, the environment 110 also includes one or more entity tracking devices 170 shown as a first entity tracking device 172, a second entity tracking device 174, and a third entity tracking device 176. In some arrangements, the entity tracking devices 170 are positioned in a fixed location within the environment 110.

In some arrangements, the entity tracking devices 170 are configured as RFID tags. The IoT devices are configured to receive signals (e.g., radio frequency signals) form each of the RFID tags. In these arrangements, each of the IoT devices are configured to determine which of the entity tracking devices 170 is closest to the IoT device. For example, a third IoT device associated with the third user 153 may determine, based on signals received from the RFID tags, that the nearest of the entity tracking devices 170 is the third entity tracking device 176.

In some arrangements, the IoT devices associated with the users 150 are configured as RFID tags. In these arrangements, each of the entity tracking devices 170 are configured receive signals form the RFID tags and determine, based on the signals, which of the RFID tags is nearest to the entity tracking devices 170. For example, the first entity tracking device 172 may receive a first signal from a first IoT device associated with the first user 151, a second signal form the second user 152, and a third signal from the third user 153, and determine based on the first signal, the second signal, and the third signal that the first user 151 is nearest to the first entity tracking device 172.

In some arrangements, the entity tracking devices 170 are configured to have markings viewable by a user. For example, the entity tracking devices 170 may include markings indicating that each of the users 150 should stand on or near one of the entity tracking devices 170. In some arrangements, the markings are viewable through an augmented reality display of the IoT devices associated with the users 150.

In some arrangements, the entity tracking devices 170 and/or the IoT devices are configured to communicably couple to the one or more of the sensors 120 such that the entity tracking devices 170 and/or the IoT devices can send and/or receive data associated with the users to/from the one or more sensors 120. The data may include the determination of which RFID tag is nearest to one of the entity tracking devices 170 and/or one of the IoT devices. In these arrangements, the entity tracking devices 170 and/or the IoT devices can provide the data to a computing system (e.g., the provider computing system 200 of FIG. 1) such that the computing system can determine, based on the data a behavior of the users 150. For example, the entity tracking devices 170 may determine that a first IoT device associated with the first user 151 is not near any of the entity tracking devices 170, a second IoT device associated with the second user 152 is near a second entity tracking device 174, and a third IoT devices associated with the third user 153 is near a third entity tracking device 176. The computing system may determine that the second user 152 and the third user 153 have a socially responsible behavior based on the determination made by the entity tracking devices 170. Additionally, the computing system may determine that the first user 151 has undesirable behavior based on the determination made by the entity tracking devices 170.

Figure 4:
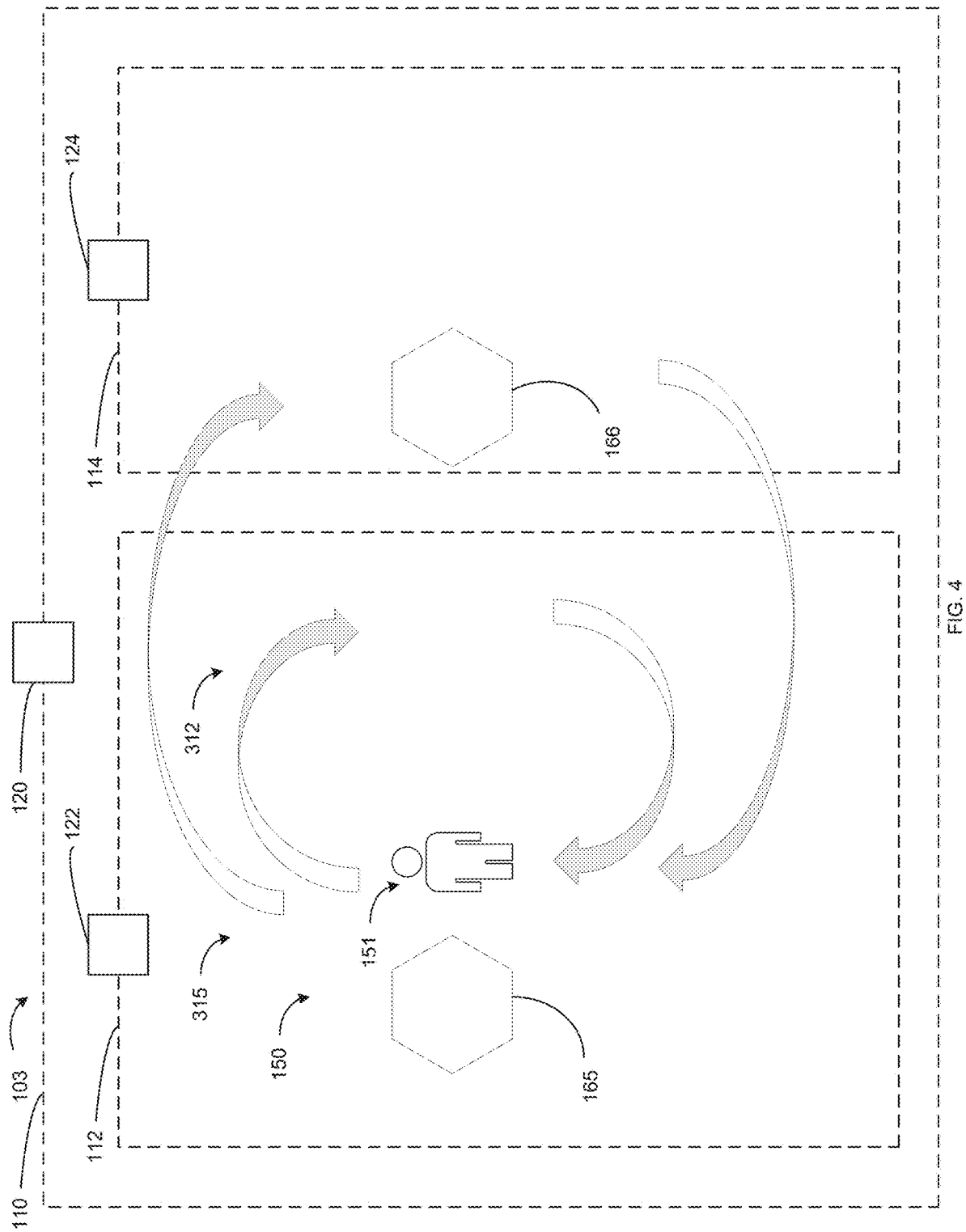
FIG. 4 is a block diagram shown an aspect related to tracking movement of a user in the environment of the system of FIG. 1, according to a fourth example arrangement.

FIG. 4 is a block diagram shown an aspect related to tracking movement of a user (e.g., first user 151) in the environment 110 of the system 100 of FIG. 1, according to a fourth example arrangement. In some arrangements, environment 110 includes one or more sensors 120 as described above. As shown, the environment 110 also includes one or more sub-environments shown as first area 112 and second area 114. The first area 112 includes one or more sensors 122, as described above. The second area 114 includes one or more sensors 124, as described above. The environment 110 also includes one or more users 150. As shown, a first user 151 is within the first area 112. In some arrangements, each of the users 150 is associated with at least one IoT device.

In some arrangements, the first area 112 is a physical location of a first business and the second area 114 is a physical location of a second business. In some arrangements, the first business has a first product 165 within the first area 112 and the second business has a second product 166 that is substantially similar to or the same as the first product 165 within the second area 114. One or more of the sensors 120, 122, 124 may sense the position of the first user 151 utilizing the devices and methods described with respect to FIGS. 1, 2, and 3 (e.g., sensors 120, 122, 124, IoT devices, mesh network 130, entity tracking devices 170, etc.) as the first user moves through the environment 110. In some arrangements, the first user 151 moves within the first area 112 defining a first path 312. As the first user 151 defines the first path 312, the first user 151 moves and/or stops near the first product 165 more than once. In some arrangements the first user 151 moves between the first area 112 and the second area 114 defining a second path 315. As the first user 151 defines the second path 315, the first user 151 moves and/or stops near the first product 165 and/or the second product 166.

In some arrangements, the sensors 120, 122, 124 are configured to communicably couple to the provider computing system 200 of FIG. 1 (e.g., via the network 105). In these arrangements, the sensors 120, 122, 124 can send data related to the position of the user 151, the first path 312 and/or the second path 315 to the provider computing system 200 of FIG. 1. The provider computing system may determine, based on the data a behavior of one or more of the users 150. For example, the provider computing system 200 may determine that the first user 151 is interested in the first product 165 and/or the second product 166 based on the first path 312 and/or the second path 315. Additionally, the provider computing system 200 may provide a particular reward token to the first user 151 based on the determination that the first user 151 is interested in the first product 165 and/or the second product 166 and that the first user 151 has a socially responsible behavior (e.g., as determined by techniques described with respect to FIGS. 1, 2, and 3). For example, the provider computing system 200 may provide a reward token including a discount for the first product 165 based on determining that the first user 151 is interested in buying the first product 165 and determine that the first user 151 has socially responsible behavior.

Figure 5:
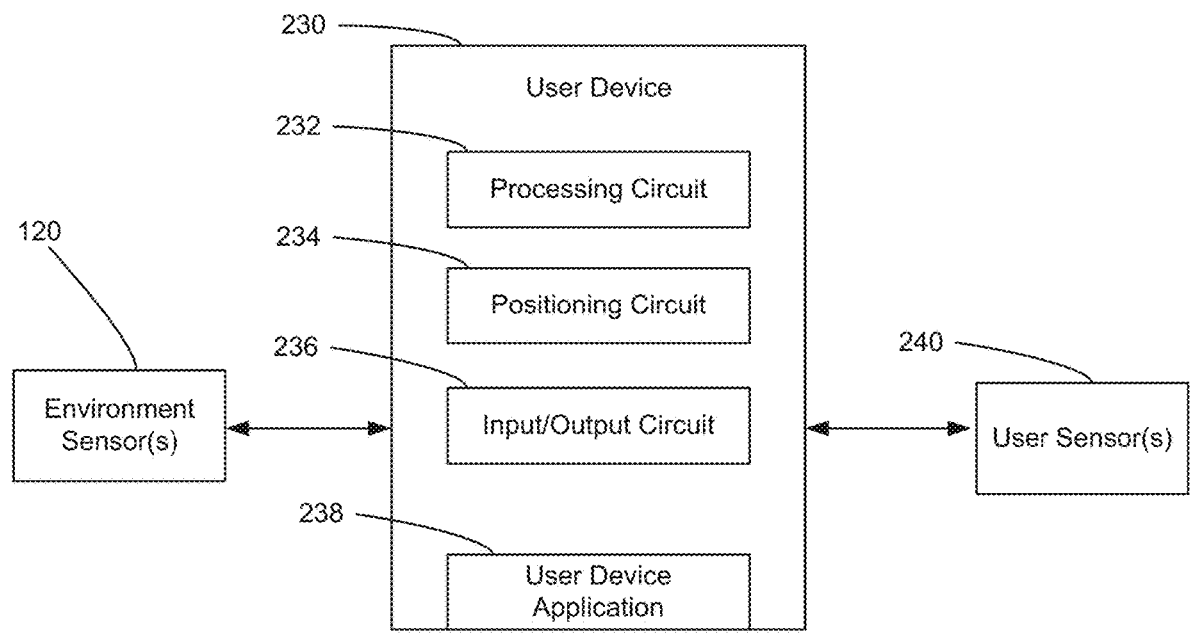
FIG. 5 is a block diagram of a user device, according to an example arrangement.

FIG. 5 is a block diagram of an IoT device configured as a user device 230, according to an example arrangement. As shown, the user device 230 includes a processing circuit 232, a position circuit 234, and an input/output circuit 236. The user device 230 also includes a user device application 238. In some arrangements, the user device 230 is configured to communicably couple to one or more environment sensors (e.g., sensors 120, 122, 124) shown as environment sensor(s) 120. In some arrangements, the user device 230 is configured to communicably couple to one or more entity positioning sensors 240.

In some arrangements, the processing circuit 232 is composed of a processor and a memory device. The processor can be implemented with a general-purpose processor, an Application Specific Integrated Circuit (ASIC), one or more Field Programmable Gate Arrays (FPGAs), a Digital Signal Processor (DSP), a group of processing components, or other suitable electronic processing components. The memory can be implemented with a Random Access Memory (RAM), Read-Only Memory (ROM), Non-volatile RAM (NVRAM), Flash Memory, hard disk storage, cloud storage, and other suitable electronic storage devices. The memory stores data and/or computer code for facilitating at least some of the various processes described herein. The memory includes tangible, non-transient volatile memory, or non-volatile memory. The memory stores programming logic that, when executed by the processor, controls the operations of the user device 230.

The positioning circuit 234 is structured to determine and provide current positional information, such as coordinates, of the device 230. The positioning circuit 234 comprises a receiver chip, which is an electronic circuit that may contain instructions thereon for issuing and receiving communication signals through the network 105, the sensors 120, 122, 124, the network circuits 130, 132, 134 and/or the mesh network 310. The receiver chip may be configured to receive global positioning system (GPS) signals, cellular tower signals, satellite network signals, etc. to determine the coordinates of the device 230.

The input/output circuit 236 is configured to receive input (e.g., from a user, an external device, etc.) and provide an output (e.g., graphics, sound, tactile feedback, etc.). In this regard, the input/output circuit 236 structured to exchange data, communications, instructions, etc. with the environment sensor(s) 120 and/or the entity positioning sensor(s) 240. In these arrangements, the input/output circuit 236 may be configured as a network interface. The network interface is structured for sending and receiving data over the network 105, the environment sensor(s), and/or the 5G. Accordingly, the network interface includes any of a cellular transceiver (for cellular standards such as 5G), local wireless network transceiver (for 802.11X, ZigBee, Bluetooth, Wi-Fi, or the like), wired network interface, a combination thereof (e.g., both a cellular transceiver and a Bluetooth transceiver), and/or the like.

In some arrangements, the input/output circuit 236 includes or is coupled to an input/output device such as but not limited to, a touchscreen, microphone, a camera, the entity positioning sensor(s) 240 and/or the like. In some arrangements, the input/output circuit 236 includes communication circuitry for facilitating the exchange of data, values, messages, and the like between the input/output circuit 236 and the components of the environment 110 such as the sensors 120, 122, 124 and/or the network circuits 130, 132, 134. In some arrangements, the input/output circuit 236 includes machine-readable media for facilitating the exchange of information between the input/output device and the components of the environment 110. In still another arrangement, input/output circuit 236 includes any combination of hardware components (e.g., a touchscreen), communication circuitry, and machine-readable media.

The entity positioning sensor(s) 240 are configured to sense one or more entity positioning characteristics of a user (e.g., one of the users 150). In some arrangements, the entity positioning sensor(s) 240 are coupled to or unitarily integrated with the user device 230. In some arrangements, the entity positioning sensors 240 are configured as smart devices (e.g., smart phone, smart watch, smart glasses, etc.) that are communicable coupled to the user device 230. In some arrangements, the entity positioning sensor(s) 240 are purpose built sensors configured to be worn by the user and sense one or more characteristics of one or more the users 150.

In some arrangements, the user device application 238 is a multithreaded application configured to prioritize processing tasks and perform certain tasks (e.g., long-running processes, such as web queries, saving data, downloading data, receiving data via from the input/output circuit 236, transmitting data via the input/output circuit 236, etc.) in background mode. For example, in some arrangements, such as those discussed with respect to FIGS. 1-4, the user device application 238 is configured to send and receive data associated with the users 150 to the provider computing system 200 via the network 105 and/or the sensors 120, 122, 124. Also, in some arrangements, the user device application 238 is configured to send and receive data associated with the users 150 to the network circuits 130, 132, 134 and/or the mesh network 310. In some arrangements, these processes are configured to be executed in the background so that the user is substantially unaware of these processes. In some arrangements, the user device application 238 is configured to automatically maintain the user device 230 in active mode and/or to periodically wake up the user device 230 such that the user device 230 remains active until the until the long-running process is completed. Advantageously, interruption or timing out of the long-running process is avoided. In an example arrangement, to maintain the user device 230 is active mode, one or more circuits of the user device application 238 is/are configured to monitor a system idle timer and reset it at predefined intervals (e.g., every 1 sec., every 5 sec., every 15 sec., every 30 sec.) to prevent the user device 230 from going into sleep mode and/or powering off.

Figure 6:
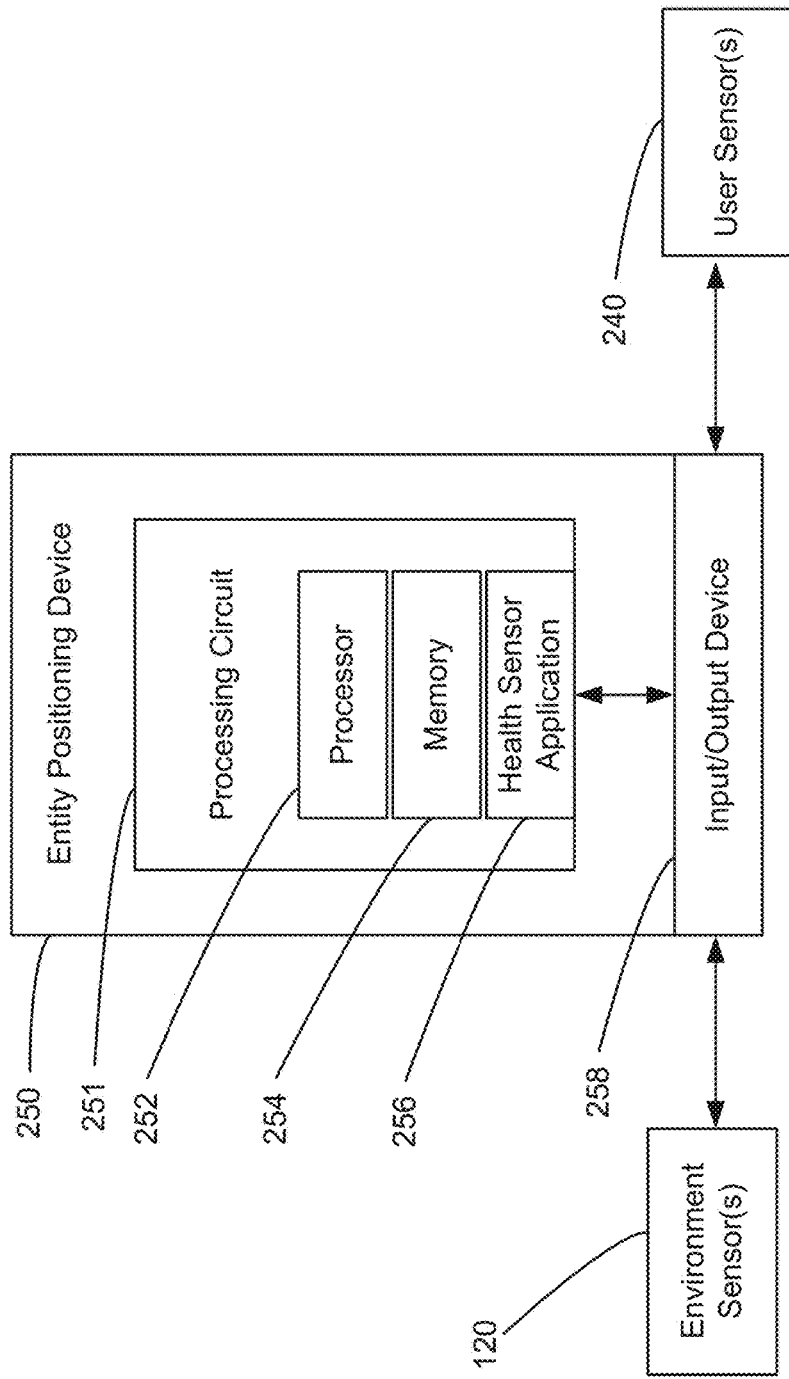
FIG. 6 is a block diagram of an entity positioning device, according to an example arrangement.

FIG. 6 is a block diagram of an IoT device configured as an entity positioning device 250, according to an example arrangement. As shown, the entity positioning device 250 includes a processing circuit 251, a position circuit and an input/output device 258. In some arrangements, the entity positioning device 250 is configured to communicably couple to one or more environment sensors (e.g., sensors 120, 122, 124) shown as environment sensor(s) 120 as described above with respect to FIG. 5. In some arrangements, the entity positioning device 250 is configured to communicably couple to one or more entity positioning sensors 240 as described above with respect to FIG. 5.

In some arrangements, the processing circuit 251 is composed of a processor 252 and a memory device 254. The processor 252 can be implemented with a general-purpose processor, an Application Specific Integrated Circuit (ASIC), one or more Field Programmable Gate Arrays (FPGAs), a Digital Signal Processor (DSP), a group of processing components, or other suitable electronic processing components. The memory 254 can be implemented with a Random Access Memory (RAM), Read-Only Memory (ROM), Non-volatile RAM (NVRAM), Flash Memory, hard disk storage, cloud storage, and other suitable electronic storage devices. The memory 254 stores data and/or computer code for facilitating at least some of the various processes described herein. The memory 254 includes tangible, non-transient volatile memory, or non-volatile memory. The memory 254 stores programming logic that, when executed by the processor 252, controls the operations of the entity positioning device 250. For example, the memory 254 may store data that includes a entity positioning application 265.

In some arrangements, the entity positioning application 265 is substantially similar to the user device application 238 discussed above with respect to FIG. 5. In particular, the entity positioning application 265 is configured to send and receive data associated with the users 150 to/from the provider computing system 200 via the network 105, the sensors 120, 122, 124, the network circuits 130, 132, 134 and/or the mesh network 310. Additionally, the entity positioning application 265 is configured to receive data associated with the users 150 from the environment sensor(s) 120 and/or the entity positioning sensor(s) 240 via the input/output device 258.

The input/output circuit 258 is configured to receive input (e.g., from a user, an external device, etc.) and provide an output (e.g., graphics, sound, tactile feedback, etc.). In this regard, the input/output circuit 258 structured to exchange data, communications, instructions, etc. with the environment sensor(s) 120 and/or the entity positioning sensor(s) 240. In these arrangements, the input/output circuit 258 may be configured as a network interface. The network interface is structured for sending and receiving data over the network 105, the environment sensor(s) 120, and/or the network circuits 130, 132, 134 of FIG. 1. Accordingly, the network interface includes any of a cellular transceiver (for cellular standards such as 5G), local wireless network transceiver (for 802.11X, ZigBee, Bluetooth, Wi-Fi, or the like), wired network interface, a combination thereof (e.g., both a cellular transceiver and a Bluetooth transceiver), and/or the like.

In some arrangements, the input/output circuit 258 includes or is coupled to an input/output device such as but not limited to, a touchscreen, microphone, a camera, the entity positioning sensor(s) 240 and/or the like. In some arrangements, the input/output circuit 236 includes communication circuitry for facilitating the exchange of data, values, messages, and the like between the input/output circuit 236 and the components of the environment 110 such as the sensors 120, 122, 124 and/or the network circuits 130, 132, 134. In some arrangements, the input/output circuit 236 includes machine-readable media for facilitating the exchange of information between the input/output device and the components of the environment 110. In still another arrangement, input/output circuit 236 includes any combination of hardware components (e.g., a touchscreen), communication circuitry, and machine-readable media.

Figure 7:
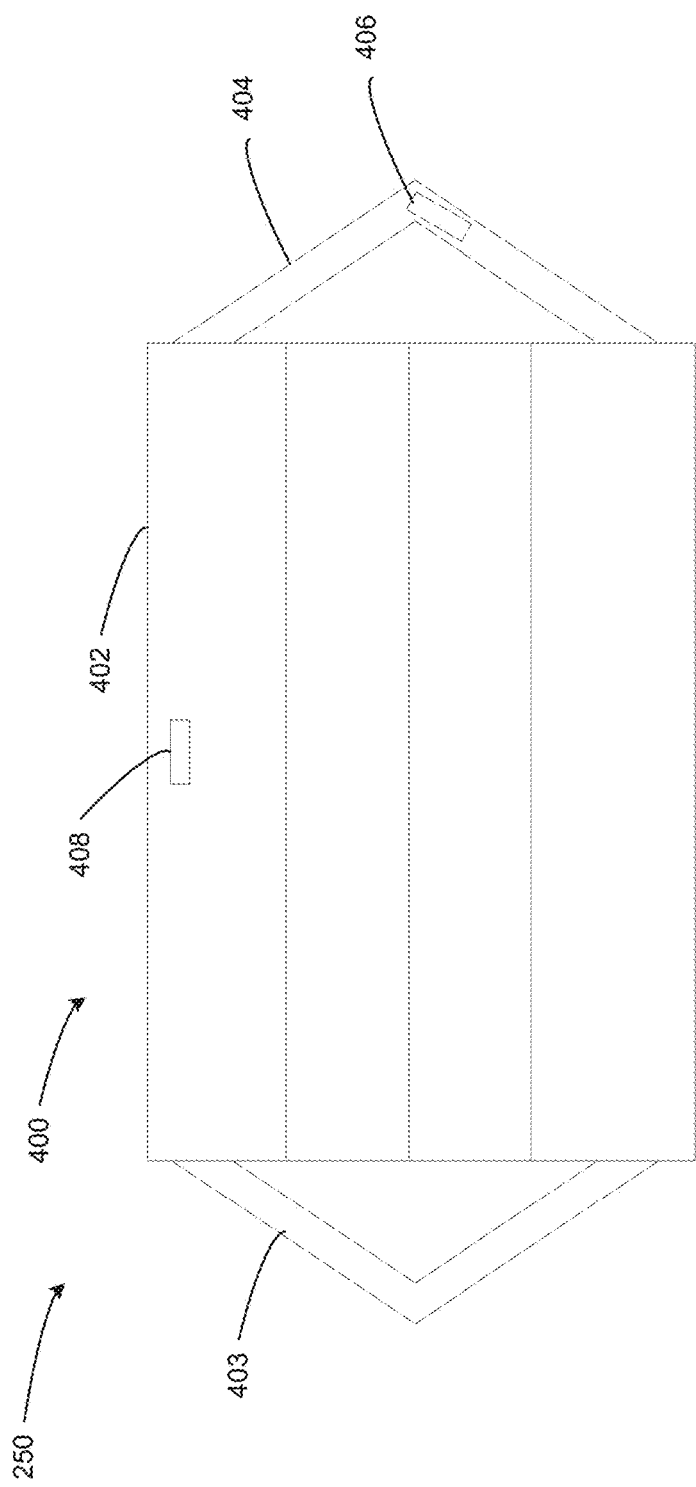
FIG. 7 is a front view of a first configuration of the entity positioning device of FIG. 6, according to an example arrangement.

FIG. 7 is a front view of a first configuration of the entity positioning device 250 of FIG. 6, according to an example arrangement. The first configuration of the entity positioning device 250 is configured as a face mask shown as mask sensor 400 configured to be worn by a user (e.g., one or more of the users 150). The mask sensor 400 includes a cover portion 402, a first ear-loop 403, a second ear-loop 404, a first sensor 406, and a second sensor 408. In some arrangements, the first sensor 406 and the second sensor 408 are substantially similar to the entity positioning sensor(s) 240 as described above with respect to FIGS. 5 and 6.

In some arrangements, the cover portion 402 has at least one membrane configured to at least partially filter air that passes through the cover portion 402. In some arrangements, the cover portion 402 is configured to be modular such that the at least one membrane can be swapped out or upgraded. The first ear-loop 403 and the second ear-loop 404 are disposed on opposite sides of the cover portion 402 and are configured to facilitate wearing mask sensor 400 by a user. For example the, first ear-loop 403 and the second ear-loop 404 may be looped around a first ear and a second ear of a user.

In some arrangements, the first sensor 406 is disposed on the second ear-loop 404. In some arrangements, the first sensor 406 is disposed on a different portion of the mask sensor 400. In some arrangements, the first sensor 406 is configured to sense one or more characteristics of a user (e.g., one of the users 150 in FIGS. 1-4) wearing the mask sensor 400 and/or one or more characteristics of the mask sensor 400. The first sensor 406 is also configured to be communicably coupled with one or more of the network 105 sensors 120, 122, 124, the network circuits 130, 132, 134, and/or the mesh network 130 as described above with respect to FIGS. 1-4. For example, the first sensor 406 may be configured as a strain gauge configured to sense strain data include a deflection of the second ear-loop 404. A computing system (e.g., the provider computing system 200 of FIG. 1) can receive the strain data and determine if a user associated with the mask sensor 400 is wearing the mask sensor 400 correctly. In some arrangements, the first sensor 406 is configured to sense if a user is wearing the mask sensor 400. In some arrangements, the first sensor 406 is configured to sense if a user is wearing the mask sensor 400 correctly.

In some arrangements, the second sensor 408 is disposed on the cover portion 408. In some arrangements, the second sensor 408 is disposed on a different portion of the mask sensor 400. In some arrangements, the first sensor 406 is configured to sense one or more characteristics of a user (e.g., one of the users 150 in FIGS. 1-4) wearing the mask sensor 400 and/or one or more characteristics of the mask sensor 400. In some arrangements, the user is associated with the mask sensor 400. In some arrangements, the user is not associated with the mask sensor 400. The second sensor 408 is also configured to be communicably coupled with one or more of the network 105 sensors 120, 122, 124, the network circuits 130, 132, 134, and/or the mesh network 130 as described above with respect to FIGS. 1-4.

In some arrangements, second sensor 408 may include an air flow sensor to sense air flowing through the cover portion 408 and output respiration data. In some arrangements, the respiration data includes a respiration pattern of a first user associated with the mask sensor 400. In some arrangements, a computing system (e.g., the provider computing system 200 of FIG. 1) can receive the respiration data and determine the respiration pattern based on the respiration data. In some arrangements, the computing system can determine if a user associated with the mask sensor 400 is wearing the mask sensor 400 correctly.

In some arrangements, the second sensor 408 is configured as a camera. The camera may be configured to capture images of one or more users. In some arrangements, a computing system (e.g., the provider computing system 200 of FIG. 1) can receive the images and determine a distance between a first user associated with the mask sensor 400 and a second user not associated with the mask sensor 400.

Figure 8:
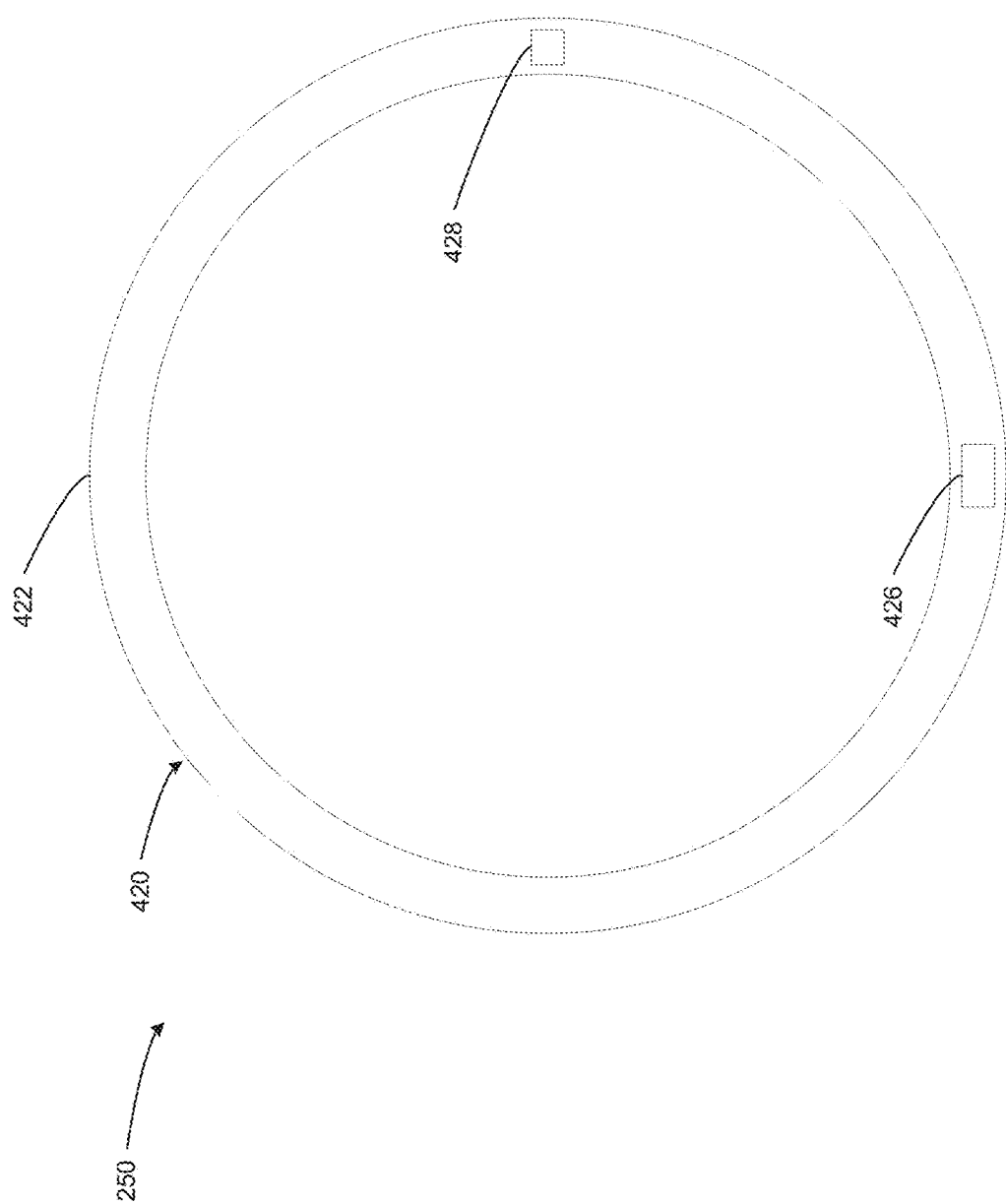
FIG. 8 is a top view of a second configuration of the entity positioning device of FIG. 6, according to an example arrangement.

FIG. 8 is a top view of a second configuration of the entity positioning device 250 of FIG. 6, according to an example arrangement. As shown, entity positioning device 250 is configured as a necklace sensor 420 configured to be worn by a user (e.g., one or more of the users 150). The necklace sensor 420 includes a band portion 422, a first sensor 426, and a second sensor 428. In some arrangements, the first sensor 426 and the second sensor 428 are substantially similar to the entity positioning sensor(s) 240 as described above with respect to FIGS. 5 and 6.

In some arrangements, the band portion 422 is configured to fit around a neck of the user. In some arrangements, the band portion 422 is configured to have a coupling component (e.g., a clasp, a hook and loop, etc.) configured to facilitate donning the necklace sensor 420.

In some arrangements, the first sensor 426 is disposed a bottom portion of the necklace sensor 420. In some arrangements, the first sensor 426 is disposed on a different portion of the necklace sensor 420. In some arrangements, the first sensor 426 configured to sense one or more characteristics of a user (e.g., the users 150 of FIGS. 1-4). In some arrangements, the user is associated with the necklace sensor 420. In some arrangements, the user is not associated with the necklace sensor 420. The first sensor 426 is also configured to be communicably coupled with one or more of the network 105 sensors 120, 122, 124, the network circuits 130, 132, 134, and/or the mesh network 130 as described above with respect to FIGS. 1-4. For example, the first sensor 426 may be configured as a camera configured to capture images of one or more users. A computing system (e.g., the provider computing system 200 of FIG. 1) can receive the images and determine a distance between a first user associated with the necklace sensor 420 and a second user not associated with the necklace sensor 420.

In some arrangements, the second sensor 428 is disposed on a first side of the band portion 422. In some arrangements, the second sensor 428 is disposed on a different portion of the necklace sensor 420. The second sensor 428 is configured to sense one or more characteristics of a user (e.g., the users 150 of FIGS. 1-4). In some arrangements, the user is associated with the necklace sensor 420. In some arrangements, the user is not associated with the necklace sensor 420. The second sensor 428 is also configured to be communicably coupled with one or more of the network 105 sensors 120, 122, 124, the network circuits 130, 132, 134, and/or the mesh network 130 as described above with respect to FIGS. 1-4. For example, the second sensor 428 may include a temperature sensor configured to sense a temperature data of a first user associated with the necklace sensor 420. A computing system (e.g., the provider computing system 200 of FIG. 1) can receive the temperature data and determine if a user associated with the necklace sensor 420 has an elevated temperature.

Figure 9:
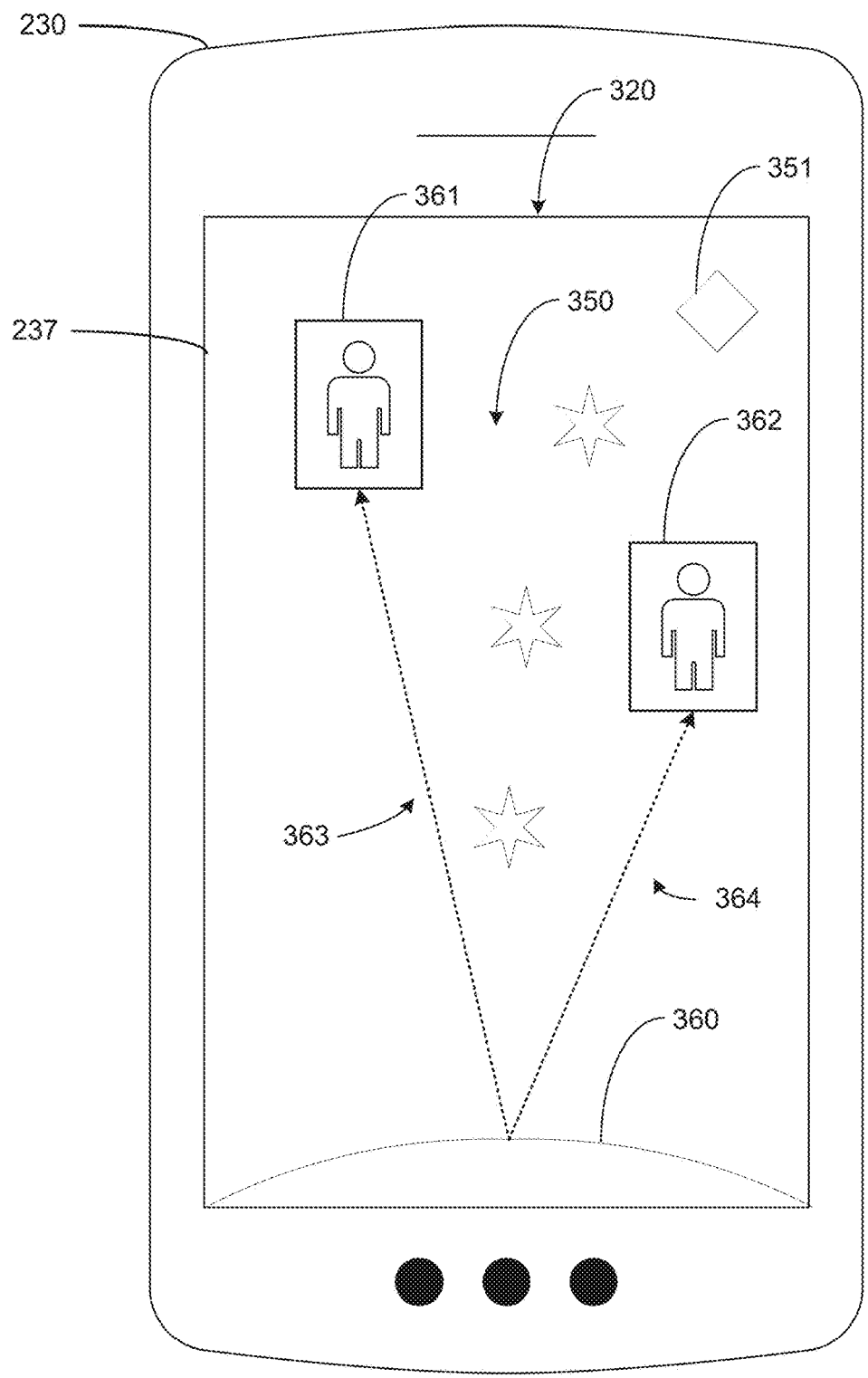
FIG. 9 is a first user interface display of the user device of FIG. 5, according to an example arrangement.

FIG. 9 is a first user interface 320 provided on a display 237 of the user device 230 of FIG. 5, according to an example arrangement. In some arrangements, the first user interface 320 is configured to display various icons depicting a distance between one or more entities including users (e.g., the users 150 in FIGS. 1-4). In some arrangements, the user device application 238, described above with respect to FIG. 5, is configured to provide the first user interface 320 on the display 237 For example and as shown in FIG. 9, a first user icon 360 represents the approximate location of a first user associated with the user device 230. A second user icon 351 represents the approximate location of a second user that is not associated with the user device 230. A third user icon 362 represents the approximate location of a third user that is not associated with the user device 230. A first distance icon 363 represents a first distance from the first user icon 360 to the second user icon 361. The first distance may be calculated by the user device 230 and/or by using the position techniques as described above with respect to FIGS. 1-8 (e.g., sensors 120, 122, 124, mesh network 312, positioning circuit 234, user sensor(s) 240, etc.). A second distance icon 364 represents a second distance from the first user icon 360 to the third user icon 362. The second distance may be calculated by the user device 230 and/or by using the position techniques as described above with respect to FIGS. 1-8 (e.g., sensors 120, 122, 124, mesh network 312, positioning circuit 234, user sensor(s) 240, etc.). In some arrangements, the first distance icon 363 and the second distance icon 364 are color coded based on distance. For example, a first color may represent a distance associated with socially responsible behavior, and a second color may represent a distance associated with undesirable behavior.

In some arrangements, the first user interface 320 also includes a directions feature having various icons that represent a path from the first user icon 360 to a destination. The icons include path markers 350 and a destination marker 351. The path markers 350 are configured to indicate a path or route that the first user (e.g., the user represented by the first user icon 360) should take to a destination. The destination marker 351 represents the location of the destination. The destination may be a location, a product, etc. with the environment 110 of FIG. 1. In some arrangements, the path markers 350 and the destination marker 351 are digital entities that includes at least one of a particular coordinate range (e.g., a coordinate with the environment 110 of FIGS. 1-4), proximity data to various businesses (e.g., relative distances within or between first area 112 and/or second area 113), etc.

In some arrangements, the provider computing system 200 determines an optimized path for the first user to take to a destination. The provider computing system 200 may determine the optimized path based on geo-location data and/or entity positioning data received by the sensors 120, 122, 124, etc. In some arrangements, the provider computing system 200 determines an optimized path for each of the users within the environment 110. In some arrangements, each of the optimized paths are also based on the other optimized paths. That is the provider computing system 200 may determine the optimized paths to reduce traffic in a particular area and/or to facilitate distancing each of the users 150.

In some arrangements, the path markers 350 and the destination marker 351 are stored in a marker database on the provider database 220 of FIG. 1. In some arrangements, the user device 230 is configured to query the marker database based on determining when the first user's location corresponds to a particular marker of the path markers 350. The first user's location may be determined utilizing the techniques described above with respect to FIGS. 1-8 (e.g., sensors 120, 122, 124, mesh network 312, positioning circuit 234, user sensor(s) 240, etc.). In some arrangements, the user device is configured to more efficiently display the path markers 350. For example, the user device 230 may be configured to cache a first subset of the path markers 350 within 100 meters of the first user and query the cache instead of querying the marker database. Additionally, the user device 230 may be configured to cache a second subset of the path markers 350 between the first user's location and the destination marker 351 and query the cache instead of querying the marker database.

In some arrangements, the display 237 is configured as an augmented reality display, and the first user interface 320 is configured as an augmented reality user interface. In some arrangements the first user interface 320 is configured to be overlaid on a real time image taken by the user device 230 (e.g., a camera coupled the input/output circuit 236 of FIG. 5). For example, the first user icon 360, the second user icon 361, and the third user icon 362 are overlaid on images of the first user, the second user, and the third use, respectively.

Figure 10:
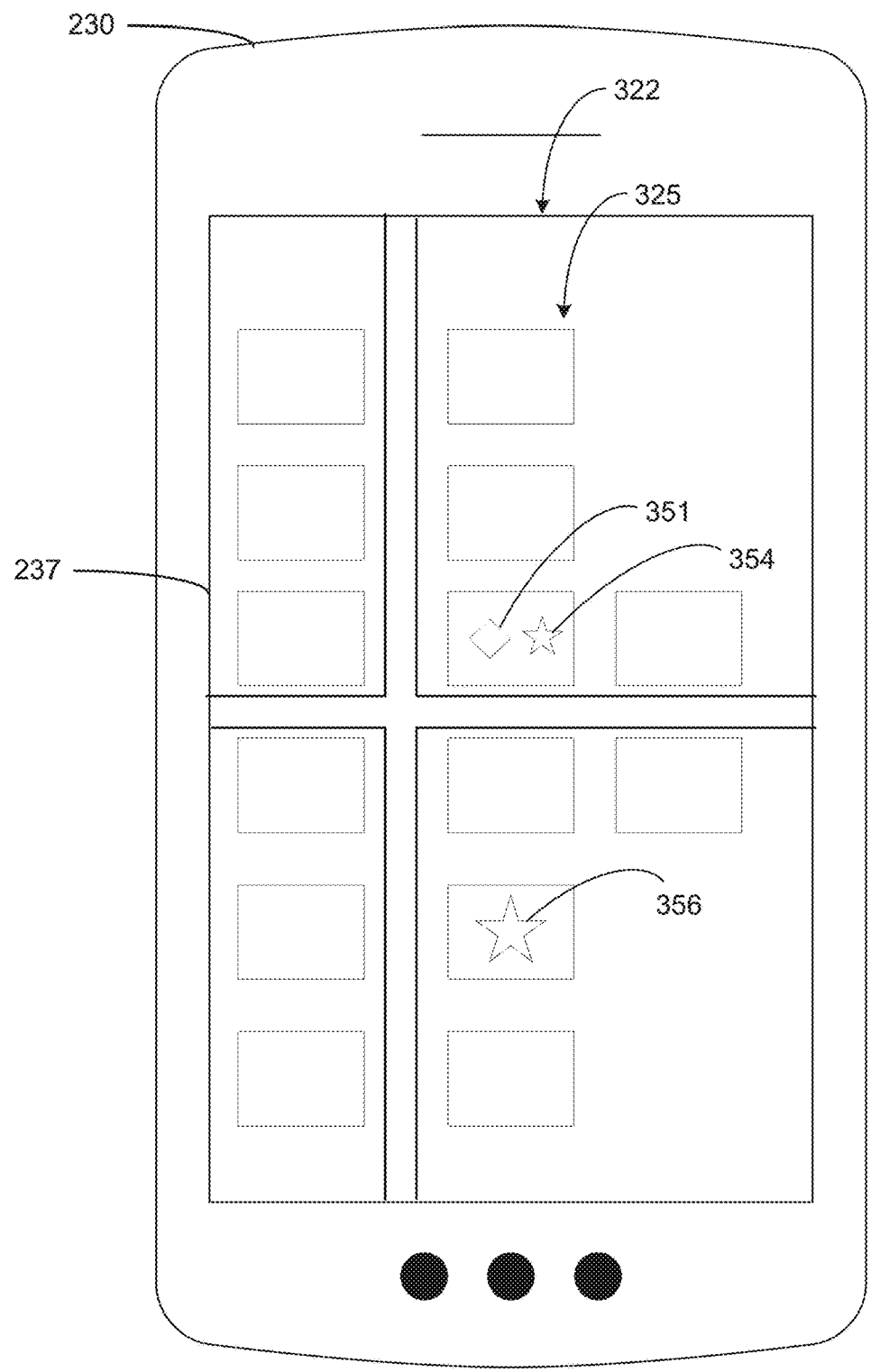
FIG. 10 is a second user interface display of the user device of FIG. 5, according to an example arrangement.

FIG. 10 is a second user interface 322 provided on a display 237 of the user device 230 of FIG. 5, according to an example arrangement. In some arrangements, the second user interface 322 is configured to display a map 325. In some arrangements, the map 325 is a map of the environment 110, the first area 112, and/or the second area 114 of FIG. 1. For example, the map 325 may be a map of an area of a city, an area of a grocery store, and the like. In some arrangements, the second user interface 322 includes a destination marker 351 that is substantially similar to the destination marker 351 of FIG. 9. In some arrangements, the second user interface 322 also includes the path makers 350 of FIG. 9. In some arrangements, the second user interface 322 also includes a first interest marker 354 and a second interest marker 356. In some arrangements, the first interest marker 354 and the second interest marker 356 indicate a destination (e.g., a product, a business, etc.) that the first user may find interesting. For example, the provider computing device 200 may determine that the first user is interested in a particular product using the techniques described above with respect to FIG. 4 and store the location of the products in the provider database 220. The user device 230 may be configured to query the provider database 220 for similar products within 1000 meters of the first user and display the first interest marker 354 and the second interest marker 356 to indicate the location of the product, business, etc.

Figure 11:
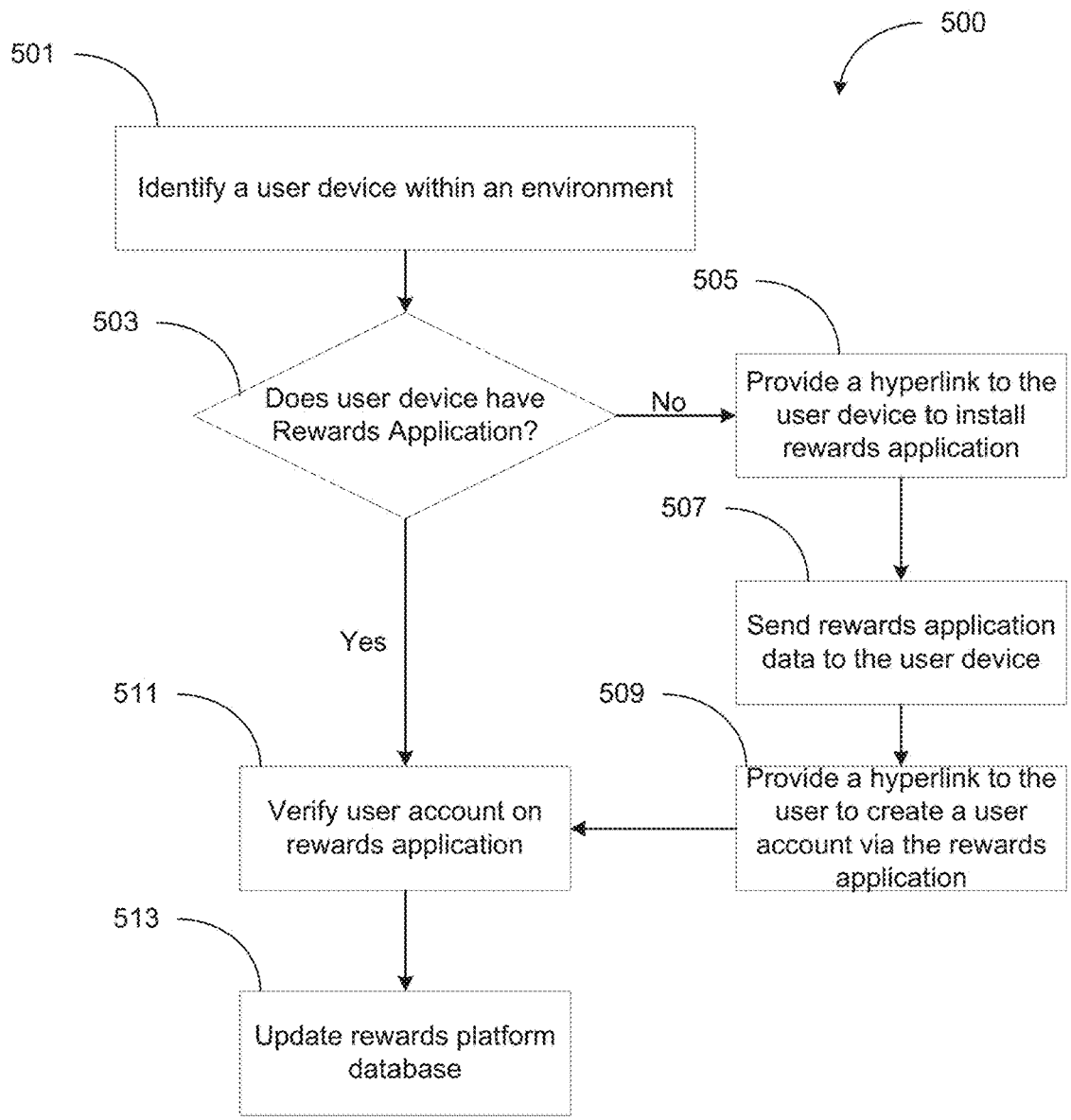
FIG. 11 is a flowchart of a method of registering a user to the system of FIG. 1, according to an example arrangement.

FIG. 11 is a flowchart of a method 500 of registering a user to the system 100 of FIG. 1, according to an example arrangement. Operations of the method 500 may be conducted by the provider computing system 200. Through operations of the method 500, the provider computing system 200 receives data from devices associated with the environment 110, the first area 112, and/or the second area 114 such as the sensors 120, 122, 124, network circuits 130, 132, 134, and/or the mesh network 310.

As shown, the method 500 begins at step 501 where the provider computing system 200 identifies a user device (e.g., user device 230 of FIG. 5) within the environment 110 the first area 112, and/or the second area 114 via one or more of the sensors 120, 122, 124, network circuits 130, 132, 134, and/or the mesh network 310.

At step 503, the provider computing system 200 determines if the user device 230 has the rewards application (e.g., the user device application 238) installed on the user device 230. If the rewards application is on the user device 230, the method proceeds to step 511. If the rewards application is not on the user device 320 the method 500 proceeds to step 505.

At step 505, the provider computing system 200 generates and provides a hyperlink to the user device 230. The hyperlink is configured to facilitate transferring rewards application data from the provider computing system 200 to the user device 230. The provider computing system 200 may provide the hyperlink via the input/output circuit 212, the input/output circuit 236, and/or the network 105, a 5G network created by the network circuits 130, 132, 134, the mesh network 310, a cellular network, Bluetooth, SMS, and the like. In some arrangements, the hyperlink is provided in a QR code configured to be sensed by a camera coupled to the input/output circuit 236 of the user device 230.

At step 507, the provider computing system 200 provides data including the rewards application to the user device 230. In some arrangements, the provider computing system 200 may provide the data based on a user interacting with the hyperlink generated at step 505.

At step 509, the provider computing system 200 generates and provides a hyperlink to the user to create a user account via the rewards application. The hyperlink is configured to facilitate creating a user account as described with respect to the account management circuit 218 of FIG. 1.

At step 511, the provider computing system 200 verifies that a user account has been created and is associated with the rewards application on the user device 230. In some arrangements, the provider computing system 200 retrieves the user account data from the account vault 224. In some arrangements, the method may return to step 509 if the provider computing system 200 cannot verify that a user account is associated with the rewards application.

At step 513, the provider computing system 200 updates the rewards platform database (e.g., the provider database 220). In some arrangements, the provider computing system 200 updates the rewards platform database with data that indicates that the user device 230 is within the environment 110 the first area 112, and/or the second area 114. In some arrangements, the provider computing system 200 updates the account vault 224 with new user account information generated at step 509.

Figure 12:
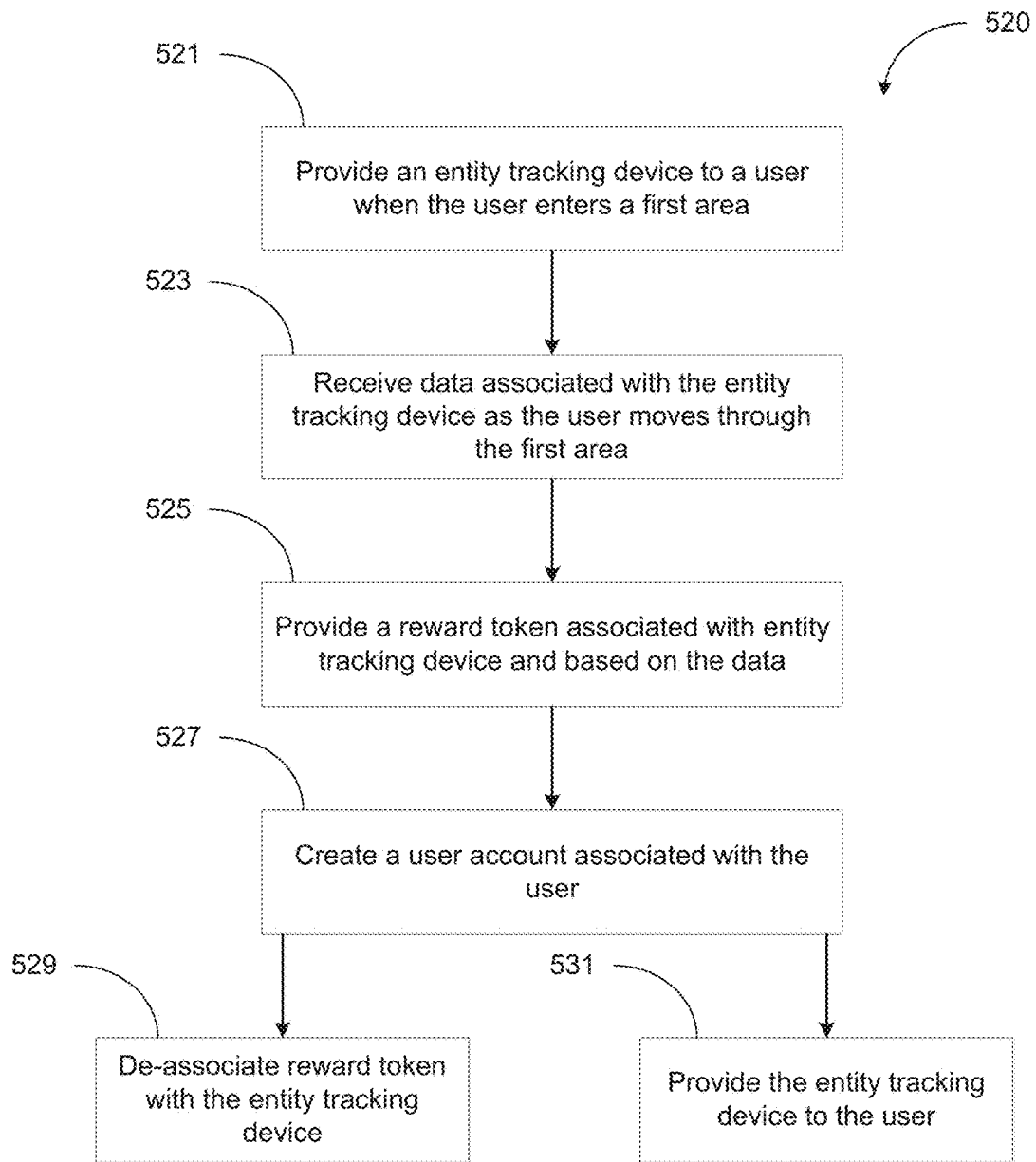
FIG. 12 is a flowchart of a method of providing the entity positioning device of FIG. 6 to a user, according to an example arrangement.

FIG. 12 is a flowchart of a method 520 of providing the entity positioning device 250 of FIG. 6 to a user (e.g., one or more of the users 150 of FIGS. 1-4), according to an example arrangement. Operations of the method 520 may be conducted by the provider computing system 200. Through operations of the method 520, the provider computing system 200 receives data from devices associated with the environment 110, the first area 112, and/or the second area 114 such as the sensors 120, 122, 124, network circuits 130, 132, 134, and/or the mesh network 310.

As shown, the method 520 begins at step 521 where an entity positioning device 250 is provided to a user (e.g., the first user 151). In some arrangements, the entity positioning device 250 is provided to the first user 151 as the first user 151 enters the environment 110 the first area 112, and/or the second area 114. In some arrangements, the entity positioning device 250 is provided to the first user 151 before the first user 151 enters the environment 110 the first area 112, and/or the second area 114. In some arrangements, the entity positioning device 250 is mailed to the first user 151 after the first user creates a first user account associated with the provider computing system 200. In some arrangements, the entity positioning device 250 is temporarily provided to the first user 151. In some arrangements, the entity positioning device 250 is temporarily provided to the first user 151 because the first user 151 does not have a user account associated with the provider computing system 200.

At step 523, the provider computing system 200 receives data associated with the entity positioning device 250. In some arrangements, the data may include at least one entity positioning characteristic of the first user 151. The at least one entity positioning characteristic may include a geo-location of the first user 151 and/or a health characteristic of the first user 151 The health characteristic may include temperature data, respiration data, and the like. The provider computing system 200 may receive the data via the input/output circuit 212, the input/output circuit 258, and/or the network 105, a 5G network created by the network circuits 130, 132, 134, the mesh network 310, etc.

At step 525, the provider computing system 200 provides a reward token and associates the reward token with the entity positioning device 250 based on the data received at step 523. In some arrangements, the reward token is generated by the token generation circuit 214. In some arrangements, the reward token is associated with the entity positioning device 250 by the reward management circuit 216. In some arrangements, the reward token is associated with the entity positioning device 250 based on a behavior of the first user 151. In some arrangements, the behavior of the first user is determine by the provider processing system 210.

Some users may want to register with the rewards system. At step 527, the provider computing system 200 creates a first user account associated with the first user such that the provider computing system 200 can associate the reward token from step 525 with the first user account. In some arrangements, the first user account is created by the account management circuit 218. In some arrangements, this can be accomplished by generating and delivering a registration hyperlink to the user's computing device. In some arrangements, when the entity positioning device 250 is not the user's computing device but rather is a physical transportation pass, museum pass, employee id card, etc., the hyperlink may be parametrized to deliver to the user's device an electronic form prompting the user to link the relevant pre-existing account corresponding to the physical device with an account on the rewards system. In some arrangements, step 527 is skipped.

Some users may not want to register with the rewards system. At step 529, the provider computing system 200 de-associates the reward token from the entity positioning device 250. For example, the token can be erased from the memory of the entity positioning device (e.g., a memory buffer can be cleared, a retrievably stored token can be erased from non-transitory memory, etc.). Any information linking the token to the individual and/or device (e.g., device identifier, location information, individual identify information) can likewise be de-associated. In some arrangements, the reward token is de-associated from the entity positioning device 250 responsive to the provider computing system 200 facilitating a transaction that includes the reward token. In some arrangements, the reward token is de-associated from the entity positioning device 250 responsive to the reward token being associated with the first user account at step 527. In some arrangements, the reward token is de-associated from the entity positioning device 250 responsive to the reward token expiring. In some arrangements, the reward token is de-associated from the entity positioning device 250 responsive to the entity positioning device 250 being returned after being temporarily provided to the first user 151.

At step 531, the provider computing system 200, the entity positioning device 250 is provided to the first user 151. In some arrangements, the entity positioning device 250 is provided permanently to the first user 151. In some arrangements, the entity positioning device 250 is provided permanently to the first user 151 responsive to the creation of a user account at step 527.

Figure 13:
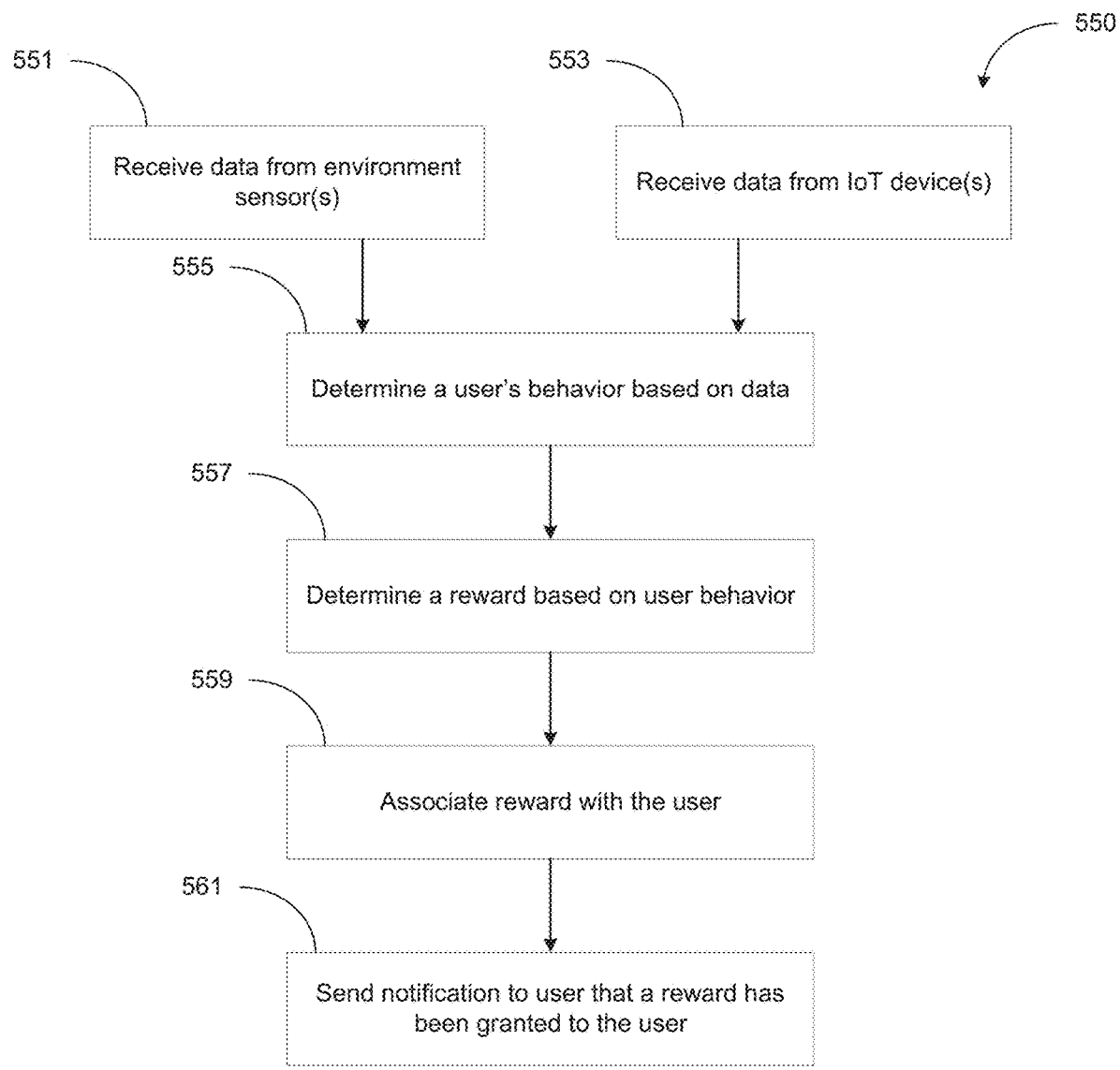
FIG. 13 is a flowchart of a method of providing a reward to a user utilizing the system of FIG. 1, according to an example arrangement.

FIG. 13 is a flowchart of a method of providing a reward to a user utilizing the system of FIG. 1, according to an example arrangement. Operations of the method 550 may be conducted by the provider computing system 200. Through operations of the method 550, the provider computing system 200 receives data from devices associated with the environment 110, the first area 112, and/or the second area 114 such as the sensors 120, 122, 124, network circuits 130, 132, 134, and/or the mesh network 310.

As shown, the method 550 begins at step 551 where the provider computing system 200 receives data from the environment sensors (e.g., sensors 120, 122, 124, etc.). As described above with respect to FIGS. 1-9, the provider computing system 200 receives data associated with one or more of the users 150 including entity positioning data such as geo-location and health data including temperature data, respiration data, and/or the like.

Similarly, at step 552, the provider computing system 200 receives data from IoT devices within the environment 110 (e.g., user device 230, entity positioning device 250, entity tracking devices 170, etc.). As described above with respect to FIGS. 1-9, the provider computing system 200 receives data associated with one or more of the users 150 including entity positioning data such as geo-location and health data including temperature data, respiration data, and/or the like.

At step 555, the provider computing system 200 determines a behavior of one or more of the uses 150 within the environment 110. In some arrangements, the behavior of the one or more users 150 is based on the data received in steps 551 and/or 553. In some arrangements, the behavior of the one or more users 150 is determined by the provider processing system 210.

At step 557, the provider computing system 200 determines a reward token for the users 150 based on the behavior. In some arrangements, the determination is made by the reward management circuit 216. As described above with respect to FIG. 1, the reward management circuit 216 may determine the type of reward token based on the behavior of the users 150. In some arrangements, the reward management circuit 216 may determine that no reward token is appropriate based on the behavior.

At step 557, the provider computing system 200 associates the reward token with the users 150. In some arrangements, the reward token is associated by the reward management circuit 216. In some arrangements, if the reward management circuit 216 may determine that no reward token is appropriate based on the behavior at step 557, the reward management circuit 216 may not associated a reward token with the users 150. Thus, the reward management circuit 216 may selectively associated a reward token with one or more of the users 150.

At step 561, the provider computing system 200 generates and sends a notification to each the users 150 that received a reward token at step 557. The notification indicates that a reward token has been granted to the users 150. In some arrangements, the notification is sent to an IoT device (e.g., user device 230, entity positioning device 250, etc.) associated with the users 150. In some arrangements, the notification is an AR based notification configured to be overlaid on a real time image captured by the IoT device.

Figure 14:
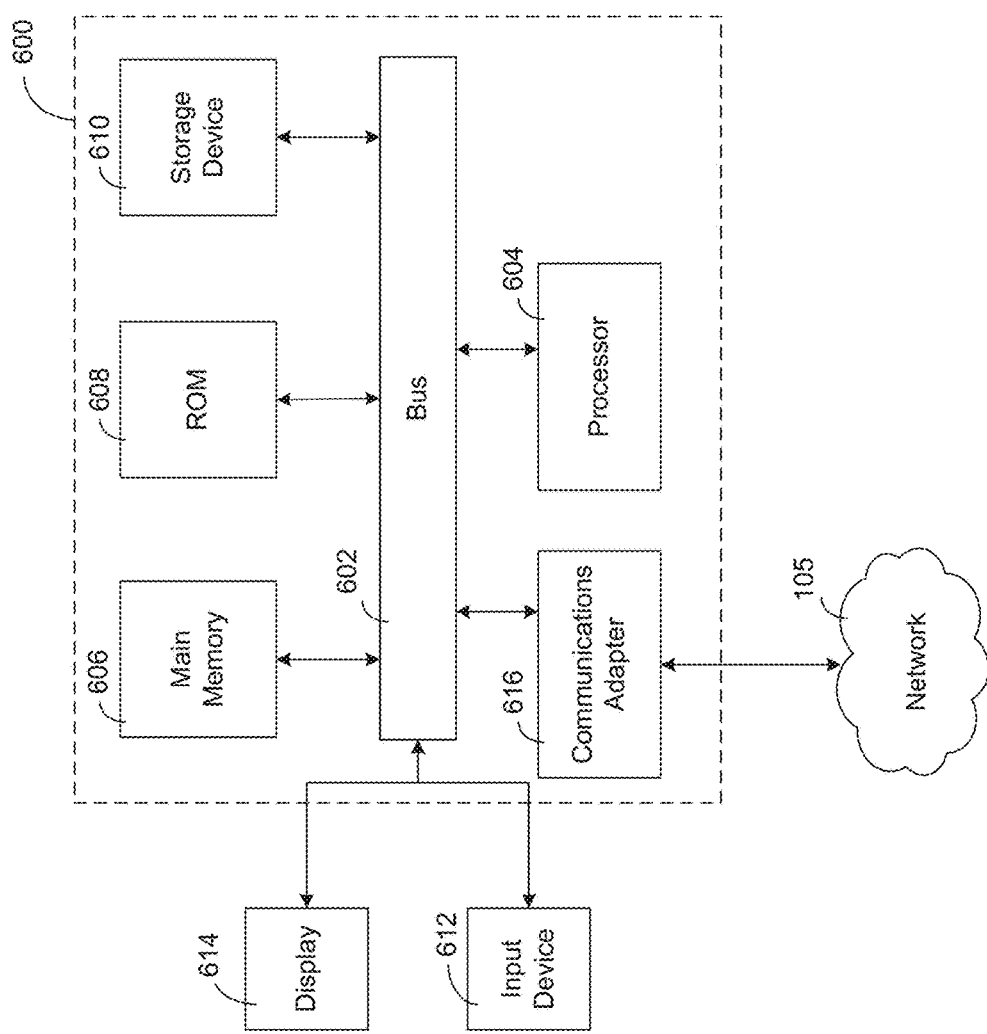
FIG. 14 is a block diagram illustrating an example computing system suitable for use in the various arrangements described herein.

Now referring to FIG. 14 depiction of a computer system 600 that can be used, for example, to implement an example provider computing system 200, an example user device 230, an example entity positioning device 250, and/or various other example systems and devices described in the present disclosure. The computing system 600 includes a bus 602 or other communication component for communicating information and a processor 604 coupled to the bus 602 for processing information. The computing system 600 also includes main memory 606, such as a random access memory (RAM) or other dynamic storage device, coupled to the bus 602 for storing information, and instructions to be executed by the processor 604. Main memory 606 can also be used for storing position information, temporary variables, or other intermediate information during execution of instructions by the processor 604. The computing system 600 may further include a read only memory (ROM) 608 or other static storage device coupled to the bus 602 for storing static information and instructions for the processor 604. A storage device 610, such as a solid state device, magnetic disk or optical disk, is coupled to the bus 602 for persistently storing information and instructions.

The computing system 600 may be coupled via the bus 602 to a display 614, such as a liquid crystal display, or active matrix display, for displaying information to a user. An input device 612, such as a keyboard including alphanumeric and other keys, may be coupled to the bus 602 for communicating information, and command selections to the processor 604. In another arrangement, the input device 612 has a touch screen display. The input device 612 can include any type of biometric sensor, a cursor control, such as a mouse, a trackball, or cursor direction keys, for communicating direction information and command selections to the processor 604 and for controlling cursor movement on the display 614.

In some arrangements, the computing system 600 may include a communications adapter 616, such as a networking adapter. Communications adapter 616 may be coupled to bus 602 and may be configured to enable communications with a computing or communications network 105 and/or other computing systems. In various illustrative arrangements, any type of networking configuration may be achieved using communications adapter 616, such as wired (e.g., via Ethernet), wireless (e.g., via WiFi, Bluetooth, etc.), satellite (e.g., via GPS) pre-configured, ad-hoc, LAN, WAN, etc.

According to various arrangements, the processes that effectuate illustrative arrangements that are described herein can be achieved by the computing system 600 in response to the processor 604 executing an arrangement of instructions contained in main memory 606. Such instructions can be read into main memory 606 from another computer-readable medium, such as the storage device 610. Execution of the arrangement of instructions contained in main memory 606 causes the computing system 600 to perform the illustrative processes described herein. One or more processors in a multi-processing arrangement may also be employed to execute the instructions contained in main memory 606. In alternative arrangements, hard-wired circuitry may be used in place of or in combination with software instructions to implement illustrative arrangements. Thus, arrangements are not limited to any specific combination of hardware circuitry and software.

The arrangements described herein have been described with reference to drawings. The drawings illustrate certain details of specific arrangements that implement the systems, methods and programs described herein. However, describing the arrangements with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As used herein, the term "circuit" may include hardware structured to execute the functions described herein. In some arrangements, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some arrangements, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexers, registers, capacitors, inductors, diodes, wiring, and so on.

The "circuit" may also include one or more processors communicatively coupled to one or more memory or memory devices. In this regard, the one or more processors may execute instructions stored in the memory or may execute instructions otherwise accessible to the one or more processors. In some arrangements, the one or more processors may be embodied in various ways. The one or more processors may be constructed in a manner sufficient to perform at least the operations described herein. In some arrangements, the one or more processors may be shared by multiple circuits (e.g., circuit A and circuit B may comprise or otherwise share the same processor which, in some example arrangements, may execute instructions stored, or otherwise accessed, via different areas of memory). Alternatively or additionally, the one or more processors may be structured to perform or otherwise execute certain operations independent of one or more co-processors. In other example arrangements, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor), microprocessor, etc. In some arrangements, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system) or remotely (e.g., as part of a remote server such as a cloud based server). To that end, a "circuit" as described herein may include components that are distributed across one or more locations.

An exemplary system for implementing the overall system or portions of the arrangements might include a general purpose computing devices in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR), EEPROM, MRAM, magnetic storage, hard discs, optical discs, etc. In other arrangements, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components), in accordance with the example arrangements described herein.

It should also be noted that the term "input devices," as described herein, may include any type of input device including, but not limited to, a keyboard, a keypad, a mouse, joystick or other input devices performing a similar function. Comparatively, the term "output device," as described herein, may include any type of output device including, but not limited to, a computer monitor, printer, facsimile machine, or other output devices performing a similar function.

Any foregoing references to currency or funds are intended to include fiat currencies, non-fiat currencies (e.g., precious metals), and math-based currencies (often referred to as cryptocurrencies). Examples of math-based currencies include Bitcoin, Litecoin, Dogecoin, and the like.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative arrangements. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps and decision steps.

The foregoing description of arrangements has been presented for purposes of illustration and description. It is not intended to be exhaustive or to limit the disclosure to the precise form disclosed, and modifications and variations are possible in light of the above teachings or may be acquired from this disclosure. The arrangements were chosen and described in order to explain the principals of the disclosure and its practical application to enable one skilled in the art to utilize the various arrangements and with various modifications as are suited to the particular use contemplated. Other substitutions, modifications, changes and omissions may be made in the design, operating conditions and arrangement of the embodiments without departing from the scope of the present disclosure as expressed in the appended claims.

What is claimed is:

1. A method of facilitating rewards for socially responsible behavior within an environment, the method comprising:
    receiving, by a provider computing system through a network via an entity positioning device associated with a first user within the environment, a first entity positioning characteristic data associated with the entity positioning device, the first entity positioning characteristic data comprising at least one of a first entity positioning geo-location data and a first entity positioning health data of the first user;
    determining, by the provider computing system, a behavior associated with the first user based on the received first entity positioning characteristic data;
    determining, by the provider computing system and based on the behavior of the first user, a first reward;
    associating, by the provider computing system, the first reward with the entity positioning device;
    identifying, by the provider computing system via an environment sensor, a first Internet of Things (IoT) device within the environment, the first IoT device associated with the first user;
    determining, by the provider computing system, whether a first IoT device application is installed on the first IoT device associated with the first user;
    providing, by the provider computing system and responsive to determining that the first IoT device application is not installed on the first IoT device, a first hyperlink to the first IoT device, the first hyperlink facilitating transferring the first IoT device application to the first IoT device;
    providing the first IoT device application to the first IoT device responsive to the first user interacting with the first hyperlink;
    providing a second hyperlink to the first IoT device via the first IoT device application, the second hyperlink configured to facilitate creating a first user account;
    determining, by the provider computing system, that the first user account has been created and that the first user account is associated with the first IoT device application on the first IoT device; and
    updating, by the provider computing system, a rewards platform database with (i) information including the first reward and (ii) information indicative of the first IoT device being within the environment.

2. The method of claim 1, further comprising:
    identifying a second IoT device within the environment;
    receiving, a second behavior data associated with the second IoT device, the second behavior data comprising at least one of a second geo-location data and a second entity positioning data;
    determining, based on the second behavior data, a second reward; and
    associating the second reward with the second IoT device.

3. The method of claim 2, wherein determining the first reward and determining the second reward further comprises:
    continuously determining a distance between the first IoT device and the second IoT device based on a first IoT geo-location data and the second geo-location data;
    increasing the first reward responsive to determining that the distance is greater than a predetermined distance; and
    decreasing the first reward responsive to determining that the distance is less than the predetermined distance.

4. The method of claim 1, further comprising providing the first user with the first reward.

5. The method of claim 4, wherein identifying the first IoT device comprises:
    providing the first user with the first IoT device when the first user enters a first area of the environment, wherein the first IoT device is configured as a first radio-frequency identification (RFID) tag;
    sensing, by at least one RFID sensor associated with the first area, a geo-location of the first RFID tag; and
    associating the geo-location of the first RFID tag with a first IoT geo-location data.

6. The method of claim 4, wherein identifying the first IoT device comprises:
    providing the first user with the first IoT device, the first IoT device is configured as a smart entity positioning tag, the smart entity positioning tag comprising:
        a geo-location device configured to determine a geo-location of the first IoT device and output a first IoT geo-location data; and at least one entity positioning sensor, each of the at least one entity positioning sensor configured to sense at least one characteristic associated with the first user and to output a first IoT entity positioning data; and associating the first IoT geo-location data with the first user and the first IoT entity positioning data with the first user.

7. The method of claim 6, wherein the first IoT entity positioning data is location detection and health data and comprises at least one of:

a temperature data collected by a first entity positioning sensor of the at least one entity positioning sensor; and a respiration data collected by a second entity positioning sensor of the at least one entity positioning sensor, the respiration data including an indication of whether the first user is wearing a mask.

8. The method of claim 1, further comprising:

sensing, by the first IoT device, a geo-location of the first IoT device;

associating the geo-location of the first IoT device with a first IoT geo-location data;

sensing, by the first IoT device, at least one characteristic associated with the first user; and associating the at least one characteristic with a first IoT entity positioning data.

9. A system for facilitating rewards for socially responsible behavior within an environment, the system comprising:

a communication interface structured to communicatively couple to a network;

an environment sensor associated with the environment;

one or more processors; and memory storing instructions that, when executed by the one or more processors, cause the one or more processors to:

receive, through the network via an entity positioning device associated with a first user within the environment, a first entity positioning characteristic data associated with the entity positioning device, the first entity positioning characteristic data comprising at least one of a first entity positioning geo-location data and a first entity positioning health data of the first user;

determine a behavior associated with the first user based on the received first entity positioning characteristic data;

determine, based on the behavior of the first user, a first reward;

associate the first reward with the entity positioning device;

identify, via the environment sensor, a first Internet of Things (IoT) device within the environment, the first IoT device associated with the first user;

determine whether a first IoT device application is installed on the first IoT device associated with the first user;

provide, responsive to determining that the first IoT device application is not installed on the first IoT device, a first hyperlink to the first IoT device, the first hyperlink facilitating transferring the first IoT device application to the first IoT device;

provide the first IoT device application to the first IoT device responsive to the first user interacting with the first hyperlink;

provide a second hyperlink to the first IoT device via the first IoT device application, the second hyperlink configured to facilitate creating a first user account;

determine that the first user account has been created and that the first user account is associated with the first IoT device application on the first IoT device; and update a rewards platform database with (i) information including the first reward and (ii) information indicative of the first IoT device being within the environment.

10. The system of claim 9, wherein the instructions further cause the one or more processors to:

identify a second IoT device within the environment;

receive, a second behavior data associated with the second IoT device, the second behavior data comprising at least one of a second geo-location data and a second entity positioning data;

determine, based on the second behavior data, a second reward; and associate the second reward with the second IoT device.

11. The system of claim 10, wherein determining the first reward and determining the second reward further comprises:

continuously determine a distance between the first IoT device and the second IoT device based on a first IoT geo-location data and the second geo-location data;

increase the first reward responsive to determining that the distance is greater than a predetermined distance; and decrease the first reward responsive to determining that the distance is less than the predetermined distance.

12. The system of claim 9, wherein the instructions further cause the one or more processors to provide the first user with the first reward.

13. The system of claim 12, wherein identifying the first IoT device comprises:

provide the first user with the first IoT device when the first user enters a first area of the environment, wherein the first IoT device is configured as a first radio-frequency identification (RFID) tag;

sense, by at least one RFID sensor associated with the first area, a geo-location of the first RFID tag; and associate the geo-location of the first RFID tag with a first IoT geo-location data.

14. The system of claim 12, wherein identifying the first IoT device comprises:

provide the first user with the first IoT device, the first IoT device is configured as a smart entity positioning tag, the smart entity positioning tag comprising:

a geo-location device configured to determine a geo-location of the first IoT device and output a first IoT geo-location data; and at least one entity positioning sensor, each of the at least one entity positioning sensor configured to sense at least one characteristic associated with the first user and to output a first IoT entity positioning data; and associate the first IoT geo-location data with the first user and the first IoT entity positioning data with the first user.

15. The system of claim 14, wherein the first IoT entity positioning data is location detection and health data and comprises at least one of:

a temperature data collected by a first entity positioning sensor of the at least one entity positioning sensor; and a respiration data collected by a second entity positioning sensor of the at least one entity positioning sensor, the respiration data including an indication of whether the first user is wearing a mask.

16. The system of claim 9, wherein the instructions further cause the one or more processors to:
- sense, by the first IoT device, a geo-location of the first IoT device;
- associate the geo-location of the first IoT device with a first IoT geo-location data;
- sense, by the first IoT device, at least one characteristic associated with the first user; and
- associate the at least one characteristic with a first IoT entity positioning data.

17. Non-transitory computer-readable storage media having instructions stored thereon that, when executed by at least one processing circuit, cause the at least one processing circuit to:
- receive, through a network via an entity positioning device associated with a first user within an environment, a first entity positioning characteristic data associated with the entity positioning device, the first entity positioning characteristic data comprising at least one of a first entity positioning geo-location data and a first entity positioning health data of the first user;
- determine a behavior associated with the first user based on the received first entity positioning characteristic data;
- determine, based on the behavior of the first user, a first reward;
- associate the first reward with the entity positioning device;
- identify, using an environment sensor associated with the environment, a first Internet of Things (IoT) device within the environment, the first IoT device associated with the first user;
- determine whether a first IoT device application is installed on the first IoT device associated with the first user;
- provide, responsive to determining that the first IoT device application is not installed on the first IoT device, a first hyperlink to the first IoT device, the first hyperlink facilitating transferring the first IoT device application to the first IoT device;
- provide the first IoT device application to the first IoT device responsive to the first user interacting with the first hyperlink;
- provide a second hyperlink to the first IoT device via the first IoT device application, the second hyperlink configured to facilitate creating a first user account;
- determine that the first user account has been created and that the first user account is associated with the first IoT device application on the first IoT device; and
- update a rewards platform database with (i) information including the first reward and (ii) information indicative of the first IoT device being within the environment.

18. The media of claim 17, wherein the media further storing instructions that, when executed by the at least one processing circuit, cause the at least one processing circuit to:
- identify a second IoT device within the environment;
- receive, a second behavior data associated with the second IoT device, the second behavior data comprising at least one of a second geo-location data and a second entity positioning data;
- determine, based on the second behavior data, a second reward;
- associate the second reward with the second IoT device.

19. The media of claim 18, wherein the media further storing instructions that, when executed by the at least one processing circuit, cause the at least one processing circuit to:
- continuously determine a distance between the first IoT device and the second IoT device based on a first IoT geo-location data and the second geo-location data;
- increase the first reward responsive to determining that the distance is greater than a predetermined distance; and
- decrease the first reward responsive to determining that the distance is less than the predetermined distance.

20. The media of claim 19, wherein identifying the first IoT device comprises:
- provide the first user with the first IoT device when the first user enters a first area of the environment, wherein the first IoT device is configured as a first radio-frequency identification (RFID) tag;
- sense, by at least one RFID sensor associated with the first area, a geo-location of the first RFID tag; and
- associate the geo-location of the first RFID tag with the first IoT geo-location data.

* * * * *